United States Patent [19]

Sakakibara

[11] Patent Number: 4,670,540

[45] Date of Patent: Jun. 2, 1987

[54] NOVEL PEPTIDE

[75] Inventor: Shumpei Sakakibara, Suita, Japan

[73] Assignee: Ajinomoto Co., Inc., Tokyo, Japan

[21] Appl. No.: 768,718

[22] Filed: Aug. 23, 1985

[30] Foreign Application Priority Data

Aug. 29, 1984 [JP] Japan .................................. 59-180000
Apr. 9, 1985 [JP] Japan .................................. 60-74759
Jun. 14, 1985 [JP] Japan .................................. 60-128052

[51] Int. Cl.⁴ ............................................. C07K 7/10
[52] U.S. Cl. ..................................... 530/324; 530/326
[58] Field of Search ....................... 530/324, 325, 350

[56] References Cited

U.S. PATENT DOCUMENTS 4,508,712  4/1985  Needleman ......................... 530/350
4,557,864  12/1985  Needleman ......................... 530/325
4,607,023  8/1986  Thibault et al. ..................... 530/324

FOREIGN PATENT DOCUMENTS 0152333  8/1985  European Pat. Off. .
0172361  2/1986  European Pat. Off. .

OTHER PUBLICATIONS

FEBS, 1268, vol. 167, No. 2, (1984), 352-357.

*Primary Examiner*—Delbert R. Phillips

*Attorney, Agent, or Firm*—Oblon, Fisher, Spivak, McClelland & Maier

[57] ABSTRACT

Peptides represented by the formula:

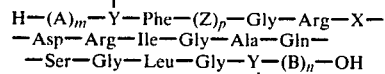

wherein:

X represents Met, Met(O), Nle, or Ile;

Y represents a cystine residue or an α-amino suberic acid residue;

Z represents Gly or Ala;

m, n, and p each represent 0 or 1;

A represents Ser, Ser-Ser, Arg-Ser-Ser, Arg-Arg-Ser-Ser, Leu-Arg-Arg-Ser-Ser, or Ser-Leu-Arg-Arg-Ser-Ser; and B represents Asn, Asn-Ser, Asn-Ser-Phe, Asn-Ser-Phe-Arg, or Asn-Ser-Phe-Arg-Tyr;

with the proviso that α-hANP(1-28), α-rANP(1-28), α-rANP(4-28), α-rANP(5-27), α-rANP(5-25), and α-rANP(3-28) are excluded from the compounds represented by the formula are disclosed along with methods of using these compounds.

3 Claims, No Drawings

NOVEL PEPTIDE

BACKGROUND OF INVENTION

1. Field of the Invention

The present invention relates to novel peptides which are useful as drugs, such as diuretic agents, therapeutic agents for hypertension, therapeutic agents for heart disease, and muscle-relaxing agents.

2. Description of the Background

Of patients with hypertension, 95% have essential hypertension, and half of these have sodium-sensitive hypertension. It is likely that sodium-sensitive hypertension is regulated as a function of Na-volume in the living body. It has been assumed that in the factors relating to natriuretic action, there is an unknown humoral factor (a third factor) in addition to GFR (glomerular filtration rate) and ardestrone. The third factor involves a substance which inhibits Na-K ATPase and one which does not inhibit it. Therefore, it has been expected that clarification of the third factor would make a significant contribution toward understanding the cause and therapy of essential hypertension.

Since the autumn of 1983, the structure of natriuretic hormone as secreted from an atrium has been established. This hormone is a third-factor substance without Na-K ATPase inhibitory activity. It possesses both strong natriuretic activity and muscle-relaxing activity. One human natriuretic peptide hormone is named α-human atrial natriuretic peptide, which is abbreviated as α-hANP, having the following structural formula:

1
H—Ser—Leu—Arg—Arg—Ser—Ser—Cys—Phe—Gly—Gly—Arg—Met—

—Asp—Arg—Ile—Gly—Ala—Gln—Ser—Gly—Leu—Gly—Cys—

28
—Asn—Ser—Phe—Arg—Tyr—OH.

One rat natriuretic peptide hormone is named α-rat atrial natriuretic peptide, which is abbreviated as α-rANP, having the following structural formula:

H—Ser—Leu—Arg—Arg—Ser—Ser—Cys—Phe—Gly—Gly—
—Arg—Ile—Asp—Arg—Ile—Gly—Ala—Gln—Ser—
—Gly—Leu—Gly—Cys—Asn—Ser—Phe—Arg—Tyr—OH

PROBLEMS SETTLED BY INVENTION

Diuretic antihypertensive drugs have been widely employed for many years as a first choice drug for the treatment of patients with hypertension. Recently, their side effects with respect to heart disease have been clarified, and new drugs having less toxicity and more positive activity have been strongly requested by clinicians.

The peptide α-hANP is assumed to be very safe because it is an endogenous factor and a peptide. However, on the other hand, because it is a peptide, there are thought to be many problems in its development as a drug. These problems include, for example, decomposition with peptidase, short duration of activity, and an unstable nature.

The inventors of the present invention have paid attention to the α-hANP peptide expecting it to be a leading compound for new drugs. They have synthesized related novel compounds and tried to develop better peptide drugs for circulatory system control.

MEANS TO SETTLE PROBLEMS

The present inventors have succeeded in the synthesis of novel peptides represented by the general formula:

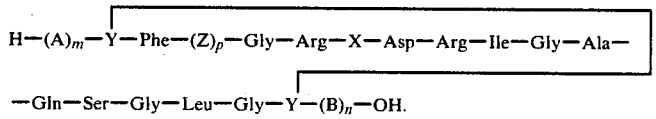

Moreover, the inventors have found that these peptides are useful as drugs, such as diuretic agents, therapeutic agents for hypertension, therapeutic agents for cardiac insufficiency, and muscle relaxants. In the formula, X represents Met, Met(0), Nle, or Ile;

represents a cystine residue (Cys Cys)

or α-amino suberic acid residue

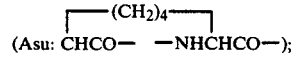

Z represents Gly or Ala; m, n, and p each represent 0 or 1; A represents Ser, Ser-Ser, Arg-Ser-Ser, Arg-Arg-Ser-Ser, Leu-Arg-Arg-Ser-Ser, or Ser-Leu-Arg-Arg-Ser-Ser; and B represents Asn, Asn-Ser, Asn-Ser-Phe, Asn-Ser-Phe-Arg, or Asn-Ser-Phe-Arg- Tyr respectively; with the proviso that α-hANP(1-28), and α-rANP(1-28), α-rANP(4-28), α-rANP(5-27), α-rANP(5-25), and α-rANP(3-28) are excluded from the compounds represented by the formula.

When the peptides of the present invention possess one or more functional groups, such as an amino group, carboxyl group, hydroxyl group, or guanidyl group, a part or all of the functional groups may be protected by a protecting group or groups used in methods for peptide synthesis or such protecting groups generally or conventionally employed in the known literature. These derivatives are included in the peptides of the present invention. Conventional means for peptide synthesis may be employed to add and remove protecting groups. Concrete examples for the peptides of the present invention are as follows:

and with an organic acid such as acetic acid or maleic acid.

Of course, when a peptide is to be included in a drug such as a diuretic, it can be in the form of a pharmaceutically acceptable salt, in addition to in the free form thereof. Non-toxicity is also required of protected derivatives.

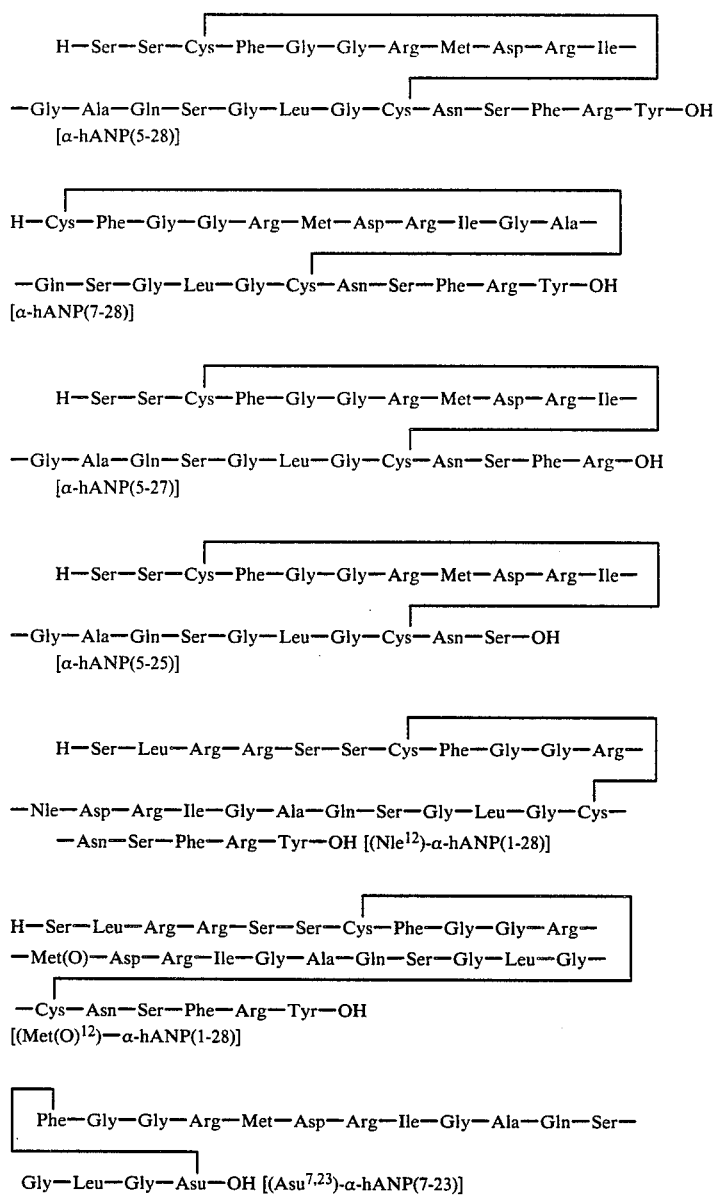

An amino acid constituting the peptide derivatives of the present invention can be either the L-isomer or the D-isomer. L-Isomers are preferred.

The peptides of the present invention can be in the form of a salt, such as a metal salt, as for example, sodium, potassium, lithium, and calcium salts, or a salt with an organic base. As the organic base, amines, such as amino (ammonium salt), dicyclohexylamine and N-methyl-D-glucamine, and basic amino acids, such as lysine and arginine, can be used.

Furthermore, the peptides of the present invention can be in the form of a salt with a mineral acid, such as hydrochloric acid, sulfuric acid, or phosphoric acid, The peptides of the present invention can be produced on the basis of the examples as mentioned later in this specification, methods conventionally employed for peptide synthesis, and methods described in the known literature, for example, Protein Chemistry, 1 Amino Acid Peptide, published by Kyoritsu Shuppan Co. (1969), which is herein incorporated by reference.

As is obvious from the examples below, peptides of the present invention can be used as drugs for the circulatory system, such as diuretics, and heart disease.

Abbreviations and abbreviated symbols as used in the present specification have the following meanings:

1. Amino acid residues

Phe=phenylalanine, Gly=glycine, Arg=arginine, Asp=aspartic acid, Ile=Isoleucine, Ala=alanine, Gln=glutamine, Ser=serine, Leu=leucine, Met=methionine, Met(O)=methionine oxide, Nle=norleucine, Cys=cysteine, Asu=α-amino suberic acid; Asn-=Asparagine, Tyr=tyrosine,

=cystine;

2. Protecting groups

Boc=t-butyloxy carbonyl, 4-CH$_3$Bzl=p-methylbenzyl, Bzl=benzyl, Tos=tosyl, Cl$_2$Bzl=2,6-dichlorobenyl, Et=ethyl, Me=methyl, Pac=phenacyl, Su=Succinimide, 3. Reagents DMF=dimethyl formamide, AcOEt=ethyl acetate, TFA=trifluoroacetic acid, Et$_2$O=ether, HOBt=1-hydroxy benzotriazole, CH$_2$Cl$_2$=dichloromethane, WSCI=water soluble carbodiimide, Ca=calcium, AcOH=acetic acid, HCl=hydrogen chloride (hydrochloric acid), TFE=trifluoroethane, NaHCO$_3$=sodium bicarbonate, n-hexane=n-hexane, TsOH=p-toluene sulfonic acid, HF=hydrogen fluoride, NaOH=sodium hydroxide, NEt$_3$=triethyl amine, MgSO$_4$=magnesium sulfate, MeOH=methanol, CHCl$_3$=chloroform, Zn=zinc, NMP=N-methyl-2-pyrolidone, P$_2$O$_5$=phosphorus pentaoxide, CH$_3$CN=acetonitrile, Na$_2$SO$_4$=sodium sulfate.

The present invention will be explained precisely in the following examples.

EXAMPLES

Example 1

Synthesis of hANP(5-27)

Synthesis of Boc-Cys(MeBzl)AsnSer(Bzl)PheArg(Tos)-OBzl (1) Synthesis of Boc-PheArg(Tos)-OBzl Boc-Phe-OH (4 g, 15 mmole), H-Arg-OBzl.TosOH (8.9 g, 15 mmole) and HOBt (2.1 g, 15.75 mmole) were dissolved in DMF (25 ml), and WSCI (12.9 ml, 15.75 mmole) was added dropwise thereto while cooling, and the thus-obtained mixture (pH=4) was stirred overnight. To the reaction solution, AcOEt (300 ml) was added thereto, and the solution was washed with 1N HCl, water and 5% NaHCO$_3$ and water, in order, and dried with Na$_2$SO$_4$. AcOEt was distilled off under reduced pressure, and the thus-obtained residue was treated with ethyl acetate, ether, and n-hexane to give an oily substance. The substance was obtained by decantation and treated with ethyl acetate and hexane to give precipitates of the object product (6.89 g, 60%).

(2) Synthesis of Boc-Ser(Bzl)PheArg(Tos)-OBzl

A mixture of Boc-PheArg(Tos)-OBzl (6.79 g, 10.2 mmole) and TFA (20 ml) was stirred for 10 minutes while cooling and then for 20 minutes at room temperature. TFA was distilled off under reduced pressure, and ether was added to the thus-obtained residue to give a precipitate. The precipitate was dried under reduced pressure for 2 hours with NaOH and then dissolved in DMF (25 ml). NEt$_3$ (1 ml) was added thereto while cooling. Next, the mixture was reacted with Boc-Ser(Bzl)-OSu (4.2 g, 10.7 mmole) for 2.5 hours. After that, NEt$_3$ [0.4 ml (total volume: 1.4 ml, 10.2 mmole)] was added thereto, and the mixture was stirred for 40 hours with an addition of a small amount of NEt$_3$.

AcOEt (250 ml) was added to the solution as obtained above, and the solution was washed with 1N HCl, water, 5% NaHCO$_3$, and water and then dried with MgSO$_4$. AcOEt was distilled off from the solution, and the thus-obtained residue was washed several times with AcOEt/ether and n-hexane by decantation. After that, by using the same steps as above, powders of the object product (7.7 g, 89.5%) were obtained.

(3) Synthesis of Boc-AsnSer(Bzl)PheArg(Tos)-OBzl

A mixture of Boc-Ser(Bzl)PheArg(Tos)-OBzl (7.6 g, 9 mmole and TFA (25 ml) was stirred for 10 minutes under cooling and then for 30 minutes at room temperature, and 6.9 N HCl/dioxane (1.6 ml, 10.8 mmole) was added therto. The solvent was distilled off under reduced pressure. To the thus-obtained residue ether was added to give powders. The powders were obtained by filtration and dried under reduced pressure for 3 hours with NaOH. The powders with Boc-Asn (2.3 g, 9.9 mmole) and HOBt (1.4 g, 9.9 mmole) were dissolved in DMF (25 ml), and WSCI (1.8 ml, 9.9 mmole) was added dropwise thereto with cooling. The thus-obtained mixture (pH=4.5) was stirred overnight mixed with ethyl acetate (200 ml); washed with 1N HCl, water, 5% NaHCO$_3$, and water; and dried with MgSO$_4$. Ethyl acetate was distilled off therefrom, and the residue was washed two times with ethyl acetate and methanol/ether to obtain powders of the object product (7.3 g, 84.9%).

(4) Synthesis of Boc-Cys(4-MeBzl)AsnSer(Bzl)PheArg(Tos)-OBzl

A mixture of Boc-AsnSer(Bzl)PheArg(Tos)-OBzl (3.8 g, 4 mmole) and TFA (15 ml) was stirred for 10 minutes while cooling and for 25 minutes at room temperature, and then 6.9 N HCl/dioxane (0.7 ml, 4.8 mmole) was added thereto. The solvent was distilled off therefrom, and to the thus-obtained residue, Et$_2$O was added. The thus precipitated powders were obtained by filtration and dried for 3.5 hours with NaOH. The powders with Boc-Cys(4-MeBzl)-OH (1.43 g, 4.4 mmole) and HOBt (595 mg, 4.4 mmole) were dissolved in DMF (15 ml), WSCI (0.81 ml, 4.4 mmole) was added dropwise thereto while cooling, and the mixture (pH=4.5) was stirred overnight; mixed with ethyl acetate (150 ml); washed with 1N HCl, water, 5% NaHCO$_3$, and water; dehydrated with toluene flashing; and treated two times with CHCl$_3$ and methanol/ether to obtain powders of the object product (4.21 g, 90.3%). Amino acid analysis [hydrolysis with 6N HCl, 108° C., 22 hours, in the presence of phenol]:

| NH$_3$ | Arg | Asp | Ser | Cys | Phe |
|---|---|---|---|---|---|
| 1.15 | 0.97 | 1.00 | 0.88 | small peak | 1.00 |

Elementary analysis Found : C 60.47%, H 6.37%, N 10.76%, Calculation : C 60.39%, H 6.36%, N 10.74%, as C$_{57}$H$_{73}$O$_{12}$N$_9$S$_2$·½H$_2$O.

Synthesis of Boc-AlaGlnSer(Bzl)GlyLeuGly-OH (5) Synthesis of Boc-Ser(Bzl)-Gly-OH Boc-Ser(Bzl)-OH (14.8 g, 50 mmole) and H-Gly-OEt.HCl (8.4 g, 60 mmole), were suspended in CH$_2$Cl$_2$ (100 ml). WSCI (10 ml, 55 mmole) was added dropwise thereto, and the mixture (pH=7) was stirred overnight.

CH$_2$Cl$_2$ was distilled off under reduced pressure, and the thus-obtained residue was dissolved in ether (300 ml) and water (50 ml). The thus-obtained solution was washed with 1 N HCl, water, 5% NaHCO$_3$, and water, and then the ether was distilled off therefrom. The thus-obtained oily substance was dissolved in MeOH (50 ml), and 1 N HaOH (50 ml, 50 mmole) was added dropwise thereto while cooling at a temperature of 0° to 1° C., and soon after a removal of the refrigerant, it was stirred at 60 minutes.

The solution was cooled again and adjusted to pH 7 with 6N HCl and methanol was distilled off. The thus-obtained residue was dissolved in aqueous NaHCO$_3$, washed 2 times with ether, and adjusted to pH 2 in the water phase with 6N HCl. The thus-obtained mixture was extracted with ethyl acetate (250 ml), washed with water, and dried with anhydrous sodium sulfate. Ethyl acetate was distilled off therefrom under reduced pressure to obtain quantitatively the object product in the oily form.

(6) Synthesis of Boc-Ser(Bzl)GlyLeuGly-OPac

A mixture of Boc-LeuGly-OPac (16.3 g, 40 mmole) and TFA (40 ml) was stirred for 10 minutes while cooling and then for 30 minutes at room temperature, and 3.5N HCl in dioxane (13.7 ml, 48 mmole) was added thereto. The solvent was distilled off therefrom, and ether-n-hexane was added to the residue to give an oil substance. The solvent was decanted, and the residual substance was pulverized with ether/n-hexane. The thus-separated powders were obtained by filtration and then dried for 3.5 hours over sodium hydroxide. The powders with Boc-Ser(Bzl)Gly-OH (total volume of the above produced oily substance) and HOBt (5.9 g, 44 mmole) were dissolved in DMF (60 ml). WSCI (18 ml, 44 mmole) was added dropwise thereto while cooling. The solution (pH=4) was stirred overnight; mixed with ethyl acetate (400 ml); washed with 1N HCl, water, 5% aqueous NaHCO$_3$, and water; and dried with anhydrous sodium sulfate. AcOEt was distilled off therefrom, and the thus-obtained residue was treated twice with AcOEt/Et$_2$O to obtain gel-like powders of the object product (19.3 g, 75.4%).

Amino acid analysis [hydrolysis with 6N HCl]

| Ser | Gly | Leu |
| --- | --- | --- |
| 0.91 | 1.00 × 2 | 1.02 |

(7) Synthesis of Boc-GlnSer(Bzl)GlyLeuGly-OPac

Boc-Ser(Bzl)GlyLeuGly-OPac (19.2 g, 30 mmole) was reacted with TFA (50 ml) for 10 minutes while cooling and then for 40 minutes at room temperature, and 3.5N HCl in dioxane (10.3 ml, 36 mmole) was added thereto. The solvent was distilled off therefrom and to the thus-obtained residue, ether/n-hexane was added. The thus-obtained powders were obtained by filtration and dried for 3 hours over NaOH. The powders with Boc-Gln-OH (8.1 g, 33 mmole) and HOBt (4.7 g, 34.5 mmole) were dissolved in DMF (50 ml). WSCI (6.3 ml, 34.5 mmole) was added dropwise thereto while cooling, and the solution (pH=4) was stirred overnight to give a solid. Water was added thereto while cooling, and the thus-obtained powders were obtained by filtration and washed with water, n-hexane, and ether. The thus-obtained powders were dissolved in warmed chloroform-methanol and then dehydrated by flashing with toluene. Chloroform-methanol was added thereto, and the thus-obtained suspension was treated twice with ether under heating to obtain the object product (22.3 g, 96.5%).

(8) Synthesis of Boc-AlaGlnSer(Bzl)GlyLeuGly-OPac

Boc-GlnSer(Bzl)GlyLeuGly-OPac (11.5 g, 15 mmole) was reacted with TFA (30 ml) for 10 minutes while cooling and then for 45 minutes at room temperature, and 6.9N HCl in dioxane (2.6 ml, 18 mmole) was added thereto. The solvent was distilled off therefrom, and to the thus-obtained residue, ether was added. The thus-obtained powders were separated by filtration and then dried for 3 hours on NaOH. The powders, together with Boc-Ala (3.1 g, 16.5 mmole) and HOBt (2.2 g, 16.5 mmole) were dissolved in DMF (30 ml). WSCI (3 ml, 16.5 mmole) was added dropwise thereto while cooling to react (pH=5). After about 30 minutes, it gave a gel throughout, was mixed with DMF (30 ml) additionally, and was then stirred overnight.

Water was added thereto while cooling, and the thus-obtained powders were separated by filtration; washed with water, n-hexane, and ether; dissolved in CHCl$_3$ and methanol; dehydrated by flashing with toluene; and purified by heating 2 times with CHCl$_3$-methanol/ether to obtain the object product (11.65 g, 92.5%).

Amino Acid analysis [hydrolysis with 6N HCl]:

| NH$_3$ | Ser | Glu | Gly | Ala | Leu |
| --- | --- | --- | --- | --- | --- |
| 1.10 | 0.93 | 1.00 | 1.02 × 2 | 1.00 | 1.01 |

Elementary analysis Found : C 58.14%, H 6.92%, N 11.57% Calculation : C 58.01%, H 6.89%, N 11.55% as C$_{41}$H$_{57}$O$_{12}$N$_7$·½H$_2$O.

(9) Synthesis of Boc-AlaGlnSer(Bzl)GlyLeuGly-OH:

Boc-AlaGlnSer(Bzl)GlyLeuGly-OPac (10.9 g, 13 mmole) was dissolved in acetic acid (100 ml) while heating and then cooled naturally. Powdered zinc (17 g) was added thereto, and the thus-obtained mixture was stirred for 50 minutes in a water bath at 43° C. The powdered zinc was removed by filtration, and acetic acid was distilled off. To the thus-obtained residue, water was added to give powders. The powders were obtained by filtration and washed with water. They are called "powder A." The mother liquor as produced above gave powders again by addition of n-hexane, and the powders were obtained by filtration and washed with ether. They are called "powder B." Powder A and powder B were combined, dissolved in heated methanol, and dehydrated by flashing with toluene. The object product (8.93 g, 95%) was obtained by reprecipitation with heated methanol/ether.

Amino acid analysis [hydrolysis with 6N HCl]:

| NH$_3$ | Ser | Glu | Gly | Ala | Leu |
| --- | --- | --- | --- | --- | --- |
| 1.16 | 0.91 | 1.00 | 1.03 × 2 | 1.00 | 1.05 |

Elementary analysis Found : C 54.45%, H 7.18%, N 13.36% Calculation : C 54.50%, H 7.15%, N 13.48% as C$_{33}$H$_{51}$O$_{11}$N$_7$·0.3H$_2$O.

(10) Synthesis of Boc-AlaGlnSer(Bzl)GlyLeuGlyCys(4-MeBzl)Asn-Ser(Bzl)PheArg(Tos)-OBzl Boc-Cys(4-MeBzl)AsnSer(Bzl)PheArg(Tos)-OBzl (1.63 g, 1.4 mmole) was reacted with TFA (5 ml) for 10 minutes while cooling and for 50 minutes at room temperature, and then 3.5N HCl in dioxane (0.48 g, 1.68 mmole) was added thereto. The solvent was distilled off, and the thus-obtained residue gave powders by addition of ether. The powders were obtained by filtration and dried for 3 hours on NaOH.

The powders together with Boc-AlaGlnSer(Bzl)-GlyLeuGly-OH (1.06 g, 1.47 mmole) and HOBt (208 mg, 1.54 mmole) were dissolved in DMF (30 ml), and WSCI (0.28 ml, 1.54 mmole) was added thereto while cooling. The thus-obtained solution (pH=4.5) was stirred overnight and then solidified. Water was added thereto while cooling. The thus-powdered substance was separated by filtration; washed with water, 5% aqueous NaHCO$_3$, water, n-hexane, and ether, in order; and dried over P$_2$O$_5$. The substance was dissolved in heated DMF (250 ml), and insoluble impurities were removed by filtration. DMF was distilled off, and the object product (2.33 g, 94%) was obtained by reprecipitation with heated DMF/methanol.

Amino acid analysis [hydrolysis with 6N HCl]:

| Arg | Asp | Ser | Glu | Gly | Ala | Cys |
|---|---|---|---|---|---|---|
| 0.95 | 1.00 | 0.84 × 2 | 0.95 | 1.00 × 2 | 0.98 | small peak |
| Leu | Phe | | | | | |
| 1.04 | 0.99 | | | | | |

Elementary analysis: Found : C, 58.92%, H, 6.60%, N, 12.55% Calculation : C, 59.10%, H, 6.50%, N, 12.68% as C$_{87}$H$_{114}$O$_{20}$N$_{16}$S$_2$.

(11) Synthesis of Boc-IleGly-OEt

Gly-OEt.HCl (9.77 g, 70.0 mmole); Boc-Ile .½H$_2$O (17.7 g, 73.5 mmole) which had been previously dissolved in CHCl$_3$ and toluene, concentrated, and dehydrated; and HOBt (9.93 g, 73.5 mmole) were dissolved in DMF (70 ml). WSCI (13.5 ml, 73.5 mmole) were added dropwise thereto while cooling and stirring. On the next day, it was confirmed that the fluorolescamine test was negative. Water was added to the reaction solution water, and the thus-obtained oily substance was separated by extraction with ethyl acetate. The ethyl acetate phase was washed with 5% aqueous NaHCO$_3$, 1N HCl, and aqueous NaCl, in order, and dried with MgSO$_4$. The ethyl acetate was distilled off, and the thus-obtained crystalline residue was recrystalized with ethyl acetate/n-hexane to obtain the objective crystals (17.5 g, 79%).

(12) Synthesis of Boc-IleGly-OH

Boc-IleGly-OEt (17.4 g, 55.5 mmole) was dissolved in methanol (60 ml), and 2N NaOH (33 ml, 66.6 mmole) was added dropwise thereto while cooling and stirring. The cooling bath was removed, and the solution was stirred for 1 hour at about 15° C. and then neutralized with 6N HCl. Methanol was distilled off, and the solution was adjusted to pH~2 and extracted with ethyl acetate. The thus-obtained ethyl acetate layer was washed with water and dried with MgSO$_4$. Ethyl acetate was distilled off therefrom,, and the thus-obtained oily residue was crystalized with ethyl acetate/n-hexane to give the object product (15.5 g, 98%).

(13) Synthesis of Boc-IleGly-OPac

Boc-IleGly-OH (15.3 g, 53.1 mmole) and Pac-Br (10.8 g, 54.2 mmole) were dissolved in DMF (50 ml), and Et$_3$N (7.4 ml, 54.2 mmole) was added dropwise thereto while cooling. After 4 hours, water was poured into the reaction solution, and the thus-obtained mixture was extracted with ethyl acetate. The ethyl acetate layer was washed with 1N HCl, water, 5% aqueous NaHCO$_3$, and water, in order, and dried with MgSO$_4$. Ethyl acetate was distilled off, and the thus-obtained residue was recrystalized with methanol/ether. Yield: 16.0 g.

The mother liquor as produced above was concentrated and gave the object product (5.4 g) was obtained by recrystallization with ethyl acetate/n-hexane. Both of the above-mentioned crystals were combined. Yield: 21.4 g (99%).

(14) Synthesis of Boc-Arg(Tos)IleGly-OPac

Boc-IleGly-OPac (14.3 g, 35.18 mmole) was treated with CF$_3$CO$_2$H (80 ml) for 10 minutes while cooling and for 50 minutes at room temperature, and then 3.5N HCl in dioxane (12.1 ml, 42.2 mmole) was added dropwise thereto. The excess acid was distilled off. The residue was crystalized by the addition of ether and n-hexane, and the thus-obtained crystals were dried on NaOH. These crystals, Boc-Arg(Tos) (15.9 g, 36.9 mmole), and HOBt (5.0 g, 36.9 mmole) were dissolved in DMF (50 ml). WSCI (16.7 ml, 36.9 mmole) was added dropwise thereto while cooling and stirring. The solution was adjusted to pH≈5 by the addition of Et$_3$N. On the next day, Boc-Arg(Tos) (1.50 g), HOBt (0.48 g), and WSCI (0.66 ml), which each correspond to 0.1 eq, were added thereto. On the following day, it was confirmed that the fluorolescamine test was negative. Water was poured into the reaction solution and the separated oily substance was obtained by extraction with ethyl acetate. The ethyl acetate phase was washed with 5% aqueous NaHCO$_3$, 1N HCl, and water, in order. Since precipitation of a gel-like material started, ethyl acetate was distilled off. Ether and n-hexane were added to the above-obtained residue to give a precipitate. The precipitate was obtained by filtration, dried, and recrystalized with methanol/ether to yield 22.0 g (87%).

(15) Synthesis of Boc-Asp(OBzl)Arg(Tos)IleGly-OPac

Boc-Arg(TOC)IleGly-OPac (21.8 g, 30.4 mmole) was treated with CF$_3$CO$_2$H (90 ml) for 10 minutes while cooling and for 50 minutes at room temperature. To this, 6.9N HCl in dioxane (5.3 ml, 36.48 mmole) was added, and excess acid was distilled off. Ether was added thereto to produce a powder, and the powdered substance was dried over NaOH. The powder as mentioned above, Boc-Asp(OBzl) (10.3 g, 31.9 mmole), and HOBt (4.31 g, 31.9 mmole) were dissolved in DMF (60 ml). WSCI (5.84 ml, 31.9 mmole) was dropwise thereto while cooling and stirring. The thus-obtained solution was adjusted to pH 4 to 5 by the addition of Et$_3$N. On the following day, Boc-Asp(OBzl) (0.30 g, 0.05 eg), HOBt (0.15 g, 0.05 eq), and WSCI (10.28 ml, 0.05 eq) were added thereto. After 2 hours, it was confirmed that the fluoroscamine test was negative. Water was poured into the mixture, and the thus-obtained mixture was extracted with ethyl acetate. The ethyl acetate layer was washed with 5% aqueous NaHCO₃, water, and aqueous saturated NaCl, in order, and dried over MgSO₄. Ethyl acetate was distilled off, and the thus-obtained solid residue was crystallized with methanol/ether to yield 27.6 g (98%).

(16) Synthesis of Boc-MetAsp(Bzl)Arg(Tos)IleGly-OPac

Boc-Asp(OBzl)Arg(Tos)IleGly-OPac (27.5 g, 29.8 mmole) was reacted with $CF_3CO_2H$ (110 ml) for 10 minutes while cooling and then for 50 minutes at room temperature. To this, 6.9N HCl/dioxane (5.2 ml, 35.8 mmole) was added. Excess acid was distilled off. The powder, which was obtained by the addition of ether, was dried over NaOH. In DMF (40 ml), 25.0 mmole of the powder produced above, Boc-Met (6.54 g, 26.3 mmole), and HOBt (3.55 g, 26.3 mmole) were dissolved. WSCI (4.80 ml, 26.3 mmole) was added dropwise thereto while cooling and stirring (pH≃5). On the following day, it was confirmed that the fluorolescamine test was negative. Water and ethyl acetate were poured into the reaction solution, and the thus-precipitated gel-like substance was obtained by filtration, washed with ether, and reprecipitated with methanol/ether to yield 25.0 g (95%).

(17) Synthesis of Boc-Arg(Tos)MetAsp(OBzl)Arg(Tos)-IleGly-OPac

Boc-MetAsp(OBzl)Arg(Tos)IleGly-OPac (24.5 g, 23.3 mmole) was treated with $CF_3CO_2H$ (100 ml) for 10 minutes while cooling and for 50 minutes at room temperature, and then 6.9N HCl/dioxane (4.1 ml, 28 mmole) was added. Excess acid was distilled off, and ether was added to produce a powder. The powder was obtained by filtration and dried over NaOH. This powder, Boc-Arg(Tos) (11.0 g, 25.6 mmole), and HOBt (3.5 g, 25.6 mmole) were dissolved in DMF (60 ml). WSCI (4.69 ml, 25.6 mmole) was added dropwise thereto while cooling and stirring (pH≃5). On the following day, it was confirmed that the fluoroscamine test was negative. Water was added to the solution thereto, and the thus-precipitated solid was obtained by filtration and washed with water and then ether. By reprecipitation with chloroform-methanol/ether, the object product was obtained. Yielded: 29.8 g (94%).

(18) Synthesis of Boc-Arg(Tos)MetAsp(OBzl)Arg(Tos)IleGly-OH

Boc-Arg(Tos)MetAsp(OBzl)Arg(Tos)IleGly-OPac (13.6 g, 10.0 mmole) was dissolved in acetic acid (50 ml) and powdered zinc (14 g) was added thereto. The thus-obtained mixture was warmed to 47° to 48° C. After 1 hour, the reaction was completed. The catalyst was removed by filtration, and then acetic acid was distilled off. Water was added, and the thus-precipitated solid substance was obtained by filtration and washed with water and then ether. It was reprecipitated two times with chloroform-methanol/ether, and the object product was obtained (11.9 g, 96%).

(19) Synthesis of Boc-Arg(Tos)MetAsp(OBzl)Arg(Tos)IleGlylAaGlnSer(Bzl)GlyLeuGlyCys(4-MeBzl)AsnSer(Bzl)PheArg(Tos)-OBzl The peptide (2.2 g, 1.25 mmole) as obtained in the above preparation (10) was treated with TFA (10 ml) for 10 minutes while cooling and for 45 minutes at room temperature, and 3.5N HCl/dioxane (0.43 ml, 1.5 mmole) was added thereto. After that, the solvent was distilled off. To the thus-obtained residue, ether was added, and the thus-obtained powder was separated by filtration and dried overnight on NaOH.

This powder, Boc-Arg(Tos)MetAsp(Bzl)Arg(Tos)IleGly-OH (1.6 g, 1.29 mmole), and HOBt (177 mg, 1.31 mmole) were dissolved in the solvent produced by mixing DFM (15 ml) and NMP (10 ml). WSCI (0.24 ml, 1.31 mmole) was added thereto while cooling and allowed to react. After 3 hours, it gelled throughout, and additional NMP (10 ml) was added. After the contents were stirred overnight, the fluoroscamine test was negative. Water was added thereto while cooling to produce a powder. The thus-powdered substance was obtained by filtration; washed with water, n-hexane and ether; and dried over $P_2O_5$. The substance was dissolved, sometimes repeatedly, with heated DMF, whose total volume was 300 ml, to remove insoluble impurities by filtration. The DMF was distilled off, and the thus-obtained residue was treated with heated DMF/methanol to give the object product (3.3 g, 91.2%) in the powder form.

(20) Synthesis of Boc-GlyGly-OPac

Boc-GlyGly-OH (98.2 g, 40 mmole) and phenacyl bromide (8.76 g, 44 mmole) were dissolved in DMF (40 ml), and Et₃N (6.16 ml, 44 mmole) was added thereto while cooling. After 5 hours, water was added to the reaction solution, and the thus-precipitated substance was obtained by extraction with ethyl acetate. The ethyl acetate layer was washed with 1N HCl, 5% aqueous NaHCO₃, and water, in order, and dried over MgSO₄. The ethyl acetate was distilled off, and the thus-obtained residue was recrystalized with ethyl acetate/n-hexane to yield 13.0 g (92.9%).

(21) Synthesis of Boc-PheGlyGly-OPac

Boc-GlyGly-OPac (12.6 g, 36 mmole) and TFA (50 ml) were mixed together and stirred for 45 minutes. TFA was distilled off, and to the thus-obtained residue, 0.9N HCl/dioxane (7.8 ml, 54 mmole) was added and then mixed well. Ether was added, and the thus-precipitated substance was obtained by filtration, dried, and suspended in DMF (80 ml). HOBt (5.35 g, 39.6 mmole), Boc-Phe-OH (10.5 g, 39.6 mmole), and WSCI (7.25 ml, 39.6 mmole) were added thereto while cooling to −15° C. After 16 hours of stirring, water was added to the reaction solution, and the precipitated substance was obtained by filtration and recrystalized with methanol to yield 15.3 g (85.5%).

(22) Synthesis of Boc-Cys(4-MeBzl)PheGlyGly-OPac

To Boc-PheGlyGly-OPac (12.4 g, 25 mmole), TFA (50 ml) was added, and the mixture was stirred for 50 minutes. TFA was distilled off, and to the thus-obtained residue, 3.5 N NCl/dioxane (10.6 ml, 37 mmole) was added and stirred well. Then ether was added. The produced precipitate was obtained by filtration, dried, and dissolved in DMF (40 ml). HOBt (3.78 g, 28 mmole), Boc-Cys(4-MeBzl)-OH (9.1 g, 28 mmole), and WSCI (5.1 ml, 28 mmole) were added to this solution while cooling to −15° C. After 16 hours' stirring, water was added to the reaction solution. The thus-precipitated substance was obtained by filtration and then recrystalized two times with methanol to yield 14.1 g (80.1%).

Amino acid analysis [hydrolysis with 6 N HCl]:

Arg: 0.98×3, Asp: 1.00×2, Ser: 0.88×2, Glu: 0.95 Gly: 1.01×3, Ala: 0.96, Cys: small peak, Met: 0.80, Ile: 0.92, Leu: 0.97, Phe: 1.00

Elementary analysis: Found: C, 56.27%, H, 6.48%, N, 13.40% Calculation: C, 56.30%, H, 6.45%, N, 13.42%.

(23) Synthesis of Boc-Ser(Bzl)Cys(4-Bzl)PheGlyGly-OPac

To Boc-Cys(4-MeBzl)PheGlyGly-OPac (12 g, 17 mmole), TFA (50 ml) was added, and the mixture was stirred for 50 minutes. TFA was distilled off, and to the thus-obtained residue, 3.5 N HCl/dioxane (7.3 ml, 25.5 mmole) was added and mixed well. Ether was added thereto, and the thus-precipitated substance was obtained by filtration, dried, and then dissolved in DMF (50 ml). HOBt (2.7 g, 20 mmole), Boc-Ser(Bzl)-OH (5.9 g, 20 mmole). WSCI (37 ml, 20 mmole) were added to this solution while cooling to $-15°$ C. After 16 hours' stirring, water was added to the reaction solution. The thus-obtained precipitate was separated by filtration and recrystalized two times with methanol to yield 12.1 g (80.7%).

(24) Synthesis of Boc-Ser(Bzl)Ser(Bzl)Cys(4-MeBzl) Phe-GlyGly-OPac

To Boc-Ser(Bzl)Cys(4-MeBzl)PheGlyGly-OPac (10 g, 11.3 mmole) , TFA (40 ml) was added, and the mixture was stirred for 50 minutes. TFA was distilled off, and to the thus-obtained residue, 3.5 N HCl/dioxane (4.8 ml, 17 mmole) was added. The mixture was stirred well, and then ether was added. The thus-precipitated substance was obtained by filtration, dried, and dissolved in DMF (30 ml). HOBt (1.69 g, 12.5 mmole), Boc-Ser(Bzl)-OH (3.7 g, 12.5 mmole). WSCI (2.3 ml, 12.5 mmole) were added to this solution while cooling to $-15°$ C. After 16 hours' stirring, water was added to the reaction solution, and the thus-precipitated substance was obtained by filtration and recrystalized twice with methanol to yield 11.0 g (91.7%).

(25) Synthesis of Boc-Ser(Bzl)Ser(Bzl)Cys(4-MeBZL)PheGlyGly-OH

Boc-Ser(Bzl)Ser(Bzl)Cys(4-MeBZL)PheGlyGly-OPac (8.25 g, 7.8 mmole) was dissolved in acetic acid (200 ml). Powdered zinc (15 g) was added thereto, and the mixture was stirred for 1 hour at 45° C. The zinc was removed by filtration and acetic acid was concentrated. To the thus-obtained residue, water was added. The thus-produced precipitate was obtained by filtration, dried, and reprecipitated with chloroform/ether to yield 7.0 g (95.5%).

Amino acid analysis [hydrolysis with 6 N HCl]:

Ser: 0.93×2, Gly: 1.02×2, Phe: 1.00, ½(Cys)₂: Small peak

(26) Synthesis of Boc-Ser(Bzl)Ser(Bzl)Cys (4-MeBzl)Phe-GlyGlyArg(Tos)MetAsp(OBzl)Arg- (Tos)IleGly-AlaGlnSer(Bzl)GlyLeuGlyCys(4MeBzyl) AsnSer(Bzl)PheArg(Tos)-OBzl Boc-Arg(Tos)MetAsp(OBzl)Arg(Tos)IleGlyAlaGlnSer(Bzl)GlyLeuGlyCys(4-MeBzl)AsnSer(Bzl)PheArg(Tos)-OBzl (2.17 g, 0.75 mmole) was treated with TFA (10 ml) for 10 minutes while cooling and for 50 minutes at room temperature, and then 3.5 N HCl/dioxane (0.26 ml, 0.9 mmole) was added thereto. The solvent was distilled off. To the residue, ether was added, and the thus-produced powder was obtained by filtration and dried overnight on NaOH. The powder, together with Boc-Ser(Bzl)Ser(Bzl)Cys(4-MeBzl)Phe-GlyGly-OH (741 mg, 0.788 mmole) and HOBt (111 mg, 0.825 mmole), was dissolved in NMP (30 ml). WSCI (150 µl, 0.825 mmole) was added thereto while cooling to allow reaction (pH=5). After 2 hours, it gelled throughout. NMP (10 ml) was added thereto and stirred overnight. Water was added while cooling to produce a powder. The thus-obtained powder was separated by filtration; washed with water, n-hexane, and ether, in order; and dried over P₂O₅. By repeatedly dissolving the powder in heated NMP (140 ml) and DMF (500 ml), insoluble impurities were removed by filtration. The DMF was distilled off, and to the residual NMP solution, methanol was added to make a gel-like powder. The powder was obtained by filtration and washed with methanol to obtain the object product (2.2 g, 80.5%).

Amino acid analysis [hydrolysis with 6 N HCl]:

Arg: 0.96 ×3, Asp: 1.03×2, Ser: 0.92×4, Glu: 1.06, Gly: 1.01×5, Ala: 1.00, Cys:small peak, Met: 0.64, Ile: 0.92, Leu: 1.03, Phe: 1.00×2

Elementary analysis: Found: C, 56.30%, H, 6.46%, N, 12.69% Calculation: C, 56.55%, H, 6.50%, N, 12.39% as $C_{181}H_{234}O_{40}N_{34}S_6 \cdot 7H_2O$.

(27) Synthesis of α-hANP(5- 27)

The protected peptide (48.3 mg, 0.13 mmole) as produced above (26) was reacted with TFA (5 ml) for 10 minutes while cooling and then for 50 minutes at room temperature, and 3.5 N HCl/dioxane (0.1 ml) was added thereto. The solvent was distilled off, and to the thus-obtained residue, ether was added to produce a powder. The powder was dried overnight on NaOH and then reacted with HF (7 ml) for 60 minutes at a temperature range of $-1$ to 0° C. in the presence of anisole (1.25 ml). The excess HF was distilled off, and the remaining substance was dissolved in about 50% acetic acid and washed three times with ether. The water was passed through the column "Dowex 1×2", AcO⁻, Volume: about 50 ml) to adsorb the object product, and it was eluted with 5% acetic acid to give crude powder (reduction product). The powder was dissolved in 1N acetic acid with urea (13 ml), and the thus-produced solution was added dropwise into 1M NH₄OAc/8M urea (pH 7.4, 117 ml) involving K₃Fe(CN)₆ (60 mg, 0.18 mmole) while adjusting the solution to pH 7.4 with 10% NH₄OH. Thirty minutes after the addition was completed, the solution was adjusted to pH 4.75 and the resin "IRA-45" (Cl⁻, 10 ml), was added thereto. The solution was passed through the column of the resin "IRA-45" (Cl⁻, 50 ml) to adsorb the product and eluted with 1N acetic acid. The thus-obtained eluant was fed through the column of the resin "HP−20" (about 100 ml), and the column was washed. It was eluted with CH₃CN/H₂O/acetic acid (8/1/1), and the obtained eluent was concentrated and freeze-dried from the 1% acetic acid to give crude powder (oxidation product, 285 mg). The product (229 mg) was purified first with "CM-C" as an eluting agent using 0.05 M (pH 4.7) →0.5 M (pH 4.8)NH₄OAc, and then it was purified with "HP−20" as an eluting agent using 0 → 23% CH₃CN/5% acetic acid. The main fraction (49 mg) in the resin "HP-20" was dissolved in TFA (3 ml). Aqueous NH₄I (40 mg per 1 ml of water; 20 µl, 5.52µ mole) was added thereto while cooling, and the mixture was stirred for 10 minutes in the cooling bath. Water and CCl₄ were added thereto while cooling using dry ice as a refrigerant, and the mixture was stirred slowly. When it was moved into the shaker, a gel started to precipitate slowly. The washing with CCl₄ was continued, and the gelled solution was fed through the column of the resin "HP-20" (about 20 ml) to desalt by elution with 5% acetic acid. It was eluted with CH₃CN/H₂O/AcOH (8/1/1), and the thus-obtained eluent was concentrated and then dissolved in 5% acetic acid. This solution was passed through the column of the resin "Dowex 1×2" (AcO−, about 25 ml) and eluted with 5% acetic acid. The eluent was freeze-dried. The product was purified with the resin "Sephadex LH20" as an eluting agent using 2N acetic acid to obtain the object product (30 mg).

Amino Acid analysis [hydrolysis with 6N HCl]:
NH₃:1.34×2, Arg: 1.03×3, Asp: 1.00 ×2, Ser: 0.93 ×4, Glu: 1.02, Gly: 1.00×5, Ala: 1.02, Cys: 0.51×2, Met: 0.63, Ile: 0.94, Ala:1.01, Cys: 1.02 ×2

Elementary analysis: Found: C, 43.31%, H, 6.73%, N, 16.49%

Calculation: C, 43.33%, H, 6.92%, N, 16.68% as $C_{97}H_{154}O_{32}N_{34}S_3 \cdot 3AcOH \cdot 15H_2O$.

Example 2

Synthesis of hANP(5-28)

(28) Synthesis of Boc-Cys(4-MeBzl)AsnSer(Bzl)PheArg (Tos)Tyr(C₂Bzl)-OBzl

Boc-Arg(Tos)-OH (2.97 g, 6.93 mmole), H-Tyr(C Tyr Cl₂Bzl)-OBzl. HCl (2.95 g, 6.3 mmole), and HOBt (936 mg, 6.93 mmole) were suspended in a mixture of CH₂Cl₁₂ (25 ml) and DMF (10 ml). WSCI (1.3 ml, 6.93 mmole) was added dropwise thereto while cooling (pH=4) to allow reaction. In about 40 minutes, it turned a homogeneous solution and was stirred overnight. Since it was confirmed that the amino acid ingredient remained in the solution by TLC analysis, Boc-Arg(Tos)-OH (270 mg, 0.63 mmole), and WSCI (115 ml, 0.63 mmole) were added thereto and the mixture was stirred for 3 hours. CH₂Cl₃ was distilled off. Ethyl acetate (150 ml) was added thereto, and the solution was washed with 1N HCl, water, 5% aqueous NaHCO₃, and water and then dried with Na₂SO₄. The ethyl acetate was distilled off, and the residual substance was washed two times with ethyl acetate/ether and n-hexane by decantation to obtain the powder of the object product (5.2 g, 98.1%).

(29) Synthesis of Boc-PheArg(Tos)Tyr(Cl₂Bzl)-OBzl

Boc-Arg(Tos)Tyr(Cl₂Bzl)-OBzl (5.1 g, 6.07 mmole) was treated with TFA (15 ml) for 10 minutes while cooling and then for 35 minutes at room temperature, and then 6.9 N HCl/dioxane (1.7 ml, 7.28 mmole) was added thereto. The solvent was distilled off, and to the residue, ether was added to make a powder. The powder was obtained by filtration and dried under reduced pressure for 3 hours on NaOH. The powder, together with Boc-Phe-OH (1.7 g, 6.37 mmole) and HOBt (902 mg, 6.68 mmole), was dissolved in DMF (20 ml). WSCI (1.22 ml, 6.68 mmole) was added dropwise thereto while cooling (pH=4.5), and the solution was stirred overnight. Ethyl acetate (150 ml) was added thereto, and the mixture was washed with 1N HCl, water, 5% aqueous NaHCO, and water and then dried with MgSO₄. Ethyl acetate was distilled off, and the residual substance was treated two times with ethyl acetate/ether and n-hexane to produce a powder and thereby give the object product (5.56 g, 92.7%).

(30) Synthesis of Boc-Ser(Bzl)PheArg(Tos)Tyr(Cl₂Bzl)OBzl:.

Boc-PheArg(Tos)Tyr(Cl₂Bzl)-OBzl (5.46 g, 5.53 mmole) was treated with TFA (15 ml) for 10 minutes while cooling for 35 minutes at room temperature, and then 6.9 N HCl/dioxane (0.96 ml, 6.64 mmole) was added thereto. The solvent was distilled off, and to the residual substance, ether was added to produce a powder. The powder was obtained by filtration and dried for 2 hours on NaOH. The powder, together with Boc-Ser(Bzl)-OH (1.8 g, 6.08 mmole) and HOBt (822 mg, 6.08 mmole), was dissolved in DMF (18 ml). WSCI (1.1 ml, 6.08 mmole) was added dropwise thereto while cooling (pH=4.5), and the solution was stirred overnight. Ethyl acetate (150 ml) was added thereto, and the solution was washed with 1N HCl, water, 5% NaHCO₃, and water and then dried with Na₂SO₄. Ethyl acetate was distilled off, and the thus-obtained residue was treated with ethyl acetate and ether to give an oily substance, which was allowed to stand overnight to crystalize. In the manner described above, it was crystalized to obtain the object product (5.47 g, 85.5%).

(31) Synthesis of Boc-AsnSer(Bzl)PheArg(Tos)Tyr(Cl₂Bzl)-OBzl

Boc-Ser(Bzl)PheArg(Tos)Tyr(Cl₂Bzl)-OBzl (5.4 g, 4.63 mmole) was reacted with TFA (15 ml) for 10 minutes while cooling and then for 40 minutes at room temperature, and then 3.5N HCl in dioxane (1.6 ml, 5.56 mmole) was added thereto. The solvent was distilled off, and to the residue, ether was added to produce a powder. The powder was obtained by filtration and dried for 5 hours on NaOH. The powder, together with Boc-Asn-OH (1.2 g, 5.09 mmole) and HOBt (688 mg, 5.09 mmole), was dissolved in DMF (20 ml). WSCI (0.93 ml, 5.09 mmole) was added dropwise thereto while cooling. The solution was dehydrated by flashing with toluene and treated two times with chloroform and methanol/ether to produce a powder and thereby give the object product (5.38 g, 90.9%).

Amino acid analysis [hydrolysis with 6 N HCl]:
NH₃:1.15, Arg: 0.97, Asp: 1.01, Ser: 0.89, Tyr: 0.94, Phe: 1.00

Elementary analysis: Found: C, 60.00%, H, 5.74%, N, 9.83% Calculation: C, 60.09%, H, 5.75%, N, 9.85% as $C_{64}H_{73}O_{13}N_9SCl_2$.

(32) Synthesis of Boc-Cys(4-MeBzl)AsnSer(Bzl)PheArg(Tos)-Tyr(Cl₂Bzl)-OBzl

Boc-AsnSer(Bzl)PheArg(Tos)Tyr(Cl₂Bzl)-OBzl (5.3 g, 4.14 mmole) was treated with TFA (20 ml) for 10 minutes while cooling and for 40 minutes at room temperature, and then 3.5 N Cl in dioxane (1.42 ml, 5 mmole) was added thereto. The solvent was distilled off, and to the thus-obtained residue, ether was added to produce a powder. The powder was obtained by filtration and dried on NaOH for 2.5 hours. The powder, together with Boc-Cys(4-MeBzl)-OH (1.48 g, 4.55 mmole) and HOBt (615 mg, 4.55 mmole), was dissolved in DMF (20 ml). WSCI (0.83 ml, 4.55 mmole) was added dropwise thereto while cooling (pH=5), and the mixture was stirred overnight. Ethyl acetate (200 ml) was added thereto, and the thus-obtained solution was washed with water to precipitate a gel. This mixture was washed with 1 N HCl, water, 5% aqueous NaHCO₃, and water; dehydrated by flashing with toluene;

and then treated two times with chloroform and methanol/ether to produce a powder and thereby give the object product (5.87 g, 95.4%).

Amino acid analysis [hydrolysis with 6N HCl]:
Arg: 0.97, Asp: 1.01, Ser: 0.85, Cys: small peak, Tyr: 0.97, Phe: 1.00

Elementary analysis: Found: C, 60.55%, H, 5.83%, N, 9.38% Calculation: C, 60.60%, H, 5.83%, N, 9.42% as $C_{75}H_{86}O_{14}N_{10}S_2Cl_2$.

(33) Synthesis of protected α-hANP(5-28)

Boc-AlaGlnSer(Bzl)GlyLeuGlyCys(4-MeBzl)Asn-Ser(Bzl) PheArg(Tos)Tyr(Cl$_2$Bzl)-OBzl

Boc-Cys(4-Me-Bzl)AsnSer(Bzl)PheArg(Tos)-Tyr(Cl$_2$Bzl)-OBzl (5.87 g, 3.95 mmole) was treated with TFA (20 ml) for 10 minutes while cooling and them for 35 minutes at room temperature, and then 3.5 NHCl in dioxane (1.35 ml, 4.74 mmole) was added thereto. The solvent was distilled off, and to the obtained residue, ether was added to produce a powder. The powder was obtained by filtration and dried for 4.5 hours on NaOH. The powder, together with the carboxylic acid constituent (3 g, 4.15 mmole) and HOBt (587 mg, 4.35 mmole), was dissolved in DMF (70 ml) WSCI (0.8 ml, 4.35 mmole) was added dropwise thereto while cooling (PH =4.5) to allow reaction. After 30 minutes, it gelled. After 3 hours, it again turned a homogenous solution and was stirred overnight. The fluorescamine test was negative (gel precipitated a little).

The mixture described above was poured into the diluted aqueous NaHCO$_3$ to produce a powder, which was obtained by filtration, washed with water, n-hexane, and ether, and then dried over P$_2$O$_5$. The powder was dissolved repeatedly with warmed DMF (total volume: 400 ml) to remove impurities. DMF was distilled off, and the residue was treated with warmed DMF/methanol to make a gel-like powder and thereby obtain the object product (7.76 g, 93.9%).

Amino acid analysis [hydrolysis with 6 N HCl]:
Arg: 0.97, Asp: 1.00, Ser: 0.90×2, Glu: 0.97, Gly: 1.01, Ala: 1.00, Cys: small peak, Leu: 1.03, Tyr: 0.88, Phe: 0.99

Elementary analysis: Found: C, 58.94%, H, 6.22%, N, 11.25% Calculation: C, 59.18%, H, 6.12%, N, 11.39% as $C_{103}H_{127}O_{22}N_{17}S_2Cl_2$.

(34) Synthesis of Boc-Arg(Tos)MetAsp(OBzl)Arg (Tos)IleGlyAlaGlnSer(Bzl)GlyLeuGlyCys(4-MeBzl)AsnSer(Bzl)PheArg(Tos)Tyr(Cl$_2$Bzl)-OBzl The peptide (5.8 g, 2.77 mmole) as produced above was treated with TFA (20 ml) for 10 minutes while cooling and for 55 minutes at room temperature, and then 3.5 N HCl in dioxane (0.95 ml, 3.32 mmole) was added thereto. The solvent was distilled off, and to the residue, ether was added to produce a powder. The powder was obtained by filtration and dried overnight on NaOH. The powder, together with the carboxylic acid constituent (3.6 g, 2.91 mmole) and HOBt (412 mg, 3.05 mmole), was dissolved in a mixture of NMP (40 ml) and DMF (25 ml) . WSCI (10.56 ml, 3.05 mmole) was added dropwise thereto while cooling to −8° C. to allow reaction. After two hours, it gelled and after 5.5 hours NMP (15 ml) was further added thereto. The mixture was stirred overnight to give a homogeneous solution, which produced a negative fluorescamine test. The solution was poured into water cooled with ice to produce a powder, which was obtained by filtration, washed with water, n-hexane, and ether, and then dried over P$_2$O$_5$. The powder was dissolved repeatedly with the warmed DMF (total volume: 400 ml) and filtered to remove the impurities. DMF was distilled off, and the thus-obtained residue was treated with DMF/methanol to give a gel like powder of the object product (8.71 g, 97.9%).

Amino acid analysis [hydrolysis with 6 N HCl]:
Arg: 0.96×3, Asp: 1.01×2, Ser: 0.91×2, Glu: 1.04, Gly: 1.02×3, Ala: 1.00, Cys:small peak, Met: 0.65, Ile: 0.92, Leu: 1.02, Tyr: 0.96, Phe: 1.00

Elementary analysis: Found: C, 56.30%, H, 6.36%, N, 12.69% Calculation: C, 56.32%, H, 6.24%, N, 12.50% as $C_{153}H_{197}O_{34}N_{29}S_5Cl_2$. 2.5H$_2$O

(35) Synthesis of Boc-Ser(Bzl)Ser(Bzl)Cys(4-MeBzl)PheGlyGlyArg-(Tos)MetAsp(OBzl)Arg(Tos) IleGlyAlaGlnSer(Bzl)-GlyLeuGlyCys(4-MeBzl)Asn-Ser(Bzl)PheArg(Tos)Tyr(Cl$_2$Bzl)-OBzl The peptide as produced above (2.4 g, 0.75 mmole) was treated with TFA (10 ml) for 10 minutes while cooling and then for 50 minutes at room temperature, and then 3.5 N HCl in dioxane (0.26 ml, 0.9 mmole) was added thereto. The solvent was distilled off, and to the residue, ether was added to produce a powder. The powder was obtained by filtration and dried overnight on NaOH. The powder, together with the carboxylic acid constituent (741 mg, 0.79 mmole) and HOBt (111 mg, 0.83 mmole), was dissolved in NMP (35 ml). WSCI (150 μl, 0.83 mmole) was added thereto while cooling (pH=5) to allow reaction. After 2 hours, it gelled, and after 5 hours NMP (10 ml) was further added thereto. The mixture was stirred overnight and showed a negative fluorescamine test. Water was added thereto while cooling, and the thus-powdered substance was obtained by filtration, washed with water, n-hexane, and ether, and then dried over P$_2$O$_5$. It was purified by treating with slightly heated DMF/methanol to give the object product (2.74 g, 91.3%).

Amino acid analysis [hydrolysis with 6 N HCl]:
Arg: 0.93×3, Asp: 1.00×2, Ser: 0.90×4, Glu: 1.04, Gly: 1.00×5, Ala: 1.0, Cys: 0.16×2, Met: 0.68, Ile: 0.93, Leu: 0.99, Tyr: 0.99, Phe: 0.97×2

Elementary analysis: Found: C, 58.40%, H, 6.24%, N, 12.14% Calculation: C, 58.56%, H, 6.16%, N, 12.13% as $C_{197}H_{247}O_{42}N_{35}S_6Cl_2$.

(36) Synthesis of α-hANP(5-28)

The protected peptide as produced above (525 mg, 0.13 mmole) was allowed to react for removal of the Boc-group in the same manner as described above in the production method for hANP(5-27). The thus-obtained powder was reacted with HF (7.9 ml) in the presence of anisole (1.4 ml) for 60 minutes at a temperature range of −2 to −1° C., and excess HF was distilled off. The thus-obtained residue was dissolved in about 50% acetic acid. The solution was washed three times with ether, passed through the column with resin "Dowex 1×2" (AcO$^-$, about 30 ml), and then eluted with 10% acetic acid to obtain the crude powder (reduction product). The powder was oxidized in the same manner as in the above-mentioned production method of the hANP(5-27) to obtain the crude powder in the oxidation form. The powder was purified by the column of CM-C using as an eluting agent 0.05 M(pH 4.7) → 0.5 M(pH 4.8) NH$_4$OAc. It was further purified by the column of the resin "HP-−20 using as an eluting agent 0 →27% CH$_3$CN/5% acetic acid and then by the column of the resin "Sephadex LH-20" using as an eluting agent 2N acetic acid to obtain the object product (42 mg).

Amino acid analysis [hydrolysis with 6 N HCl]:

$NH_3$: 1.31×2, Arg: 1.01×3, Asp: 1.00×2, Ser: 0.92×4, Glu: 0.97, Gly: 1.00 ×5, Ala: 1.00, Cys: 0.85×2, Met: 0.66, Ile: 0.92, Leu: 0.97, Tyr: 0.91, Phe: 1.00 ×2

Elementary analysis: Found: C, 45.51%, H, 6.62%, N, 16.45% Calculation: C, 45.21%, H, 6.80%, N, 16.78%.

Example 3

Synthesis of $(Nle^{12})\alpha$-hANP(1-28)

Synthesis of Boc-Arg(Tos)}NleAsp(OBzl)Arg(Tos)IleGly-OH

(37) Synthesis of Boc-NleAsp(OBzl)Arg(Tos)IleGly-OPac

Asp(OBzl)Arg(Tos)IleGly-OPac.HCl (4.14 g, 4.8 mmole), Boc-Nle.dicyclohexyl amine (2.18 g, 5.30 mmole), which had been desalted previously, and HOBt (0.69 g, 5.06 mmole) were dissolved in DMF (10 ml). WSCI (0.93 ml, 5.06 mmole) was added dropwise thereto while cooling and stirring (pH=5 to 6). On the next day, it was confirmed that the fluorescamine test was negative. Water was poured into the reaction solution and extracted with ethyl acetate. The ethyl acetate phase was washed with 5% aqueous $NaHCO_3$, water, 1N HCl, and water, in order, to precipitate a gel-like substance. Ethyl acetate was distilled off, and ether was added thereto. The thus-produced gel-like substance was obtained by filtration, washed with ether, and reprecipitated with methanol/ether to yield 4.12 g (83%).

(38) Synthesis of Boc-Arg(Tos)NleAsp(OBzl)Arg (Tos)IleGly-OPac

Boc-NleAsp(OBzl)Arg(Tos)IleGly-OPac (4.04 g, 3.9 mmole) was reacted with $CF_3CO_2H$ (18 ml) for 10 minutes while cooling and then for 50 minutes at room temperature, and 6.9 N HCl in dioxane (0.7 ml, 4.68 mmole) was added thereto. The excess acid was distilled off. To the thus-obtained residue, ether was added, and the residual powder was obtained by filtration and dried on NaOH.

This powder, Boc-Arg(Tos) (1.84 g, 4.29 mmole), and HOBt (0.58 g, 4.29 mmole), were dissolved in DMF (8 ml). WSCI (0.79 ml, 4.29 mmole) was added dropwise thereto while cooling and stirring (pH=4 to 5). On the next day, Boc-Arg(Tos) (0.1 g), HOBt (40 mg). WSCI (40 ml) were added. After 4 hours, it was confirmed that the fluorescamine test was negative. Water was added thereto, and the thus-precipitated solid was obtained by filtration, washed with water and next with ether, and reprecipitated with $CHCl_3$-methanol/ether to yield 4.8 g (91%).

(30) Synthesis of Boc-Arg(Tos)NleAsp(OBzl)Arg (Tos)IleGly-OH

Boc-Arg(Tos)NleAsp(OBzl)Arg(Tos)IleGly-OPac (3.36 g, 2.5 mmole) was dissolved in acetic acid (25 ml) and powdered zinc (3.3 g) was added thereto. The mixture was stirred for 50 minutes at 45° C. The zinc was removed by filtration, and acetic acid was distilled off. Water was added thereto, and the thus-precipitated solid was obtained by filtration, washed with water and ether, and reprecipitated with chloroform-methanol/ether to obtain the object product (2.9 g, 94.5%).

Elementary analysis: Found: C, 53.80%, H, 6.78%, N, 13.54%. Calculation: C, 54.00%, H, 6.80%, N, 13.50%.

Amino acid analysis [6 N HCl, 110° C. for 23 hours and phenol extraction]:

Arg: 0.93×2, Asp: 0.98, Gly: 1.00, Ile: 0.88, Nle: 1.0

(40) Synthesis of Boc-Arg(Tos)Ser(Bzl)Ser(Bzl)Cys(4-MeBzl)PheGlyGly-OPac

A mixture of Boc-Ser(Bzl)Ser(Bzl)Cys(4-MeBzl)Phe-GlyGly-OPac (2.5 g, 2.36 mmole) and TFA (10 ml) was stirred for 50 minutes. TFA was distilled off, and to the thus-obtained residue, 3.5 N HCl in dioxane (1 ml, 3.54 mmole) was added. After enough stirring, ether was added. The thus-produced precipitate was obtained by filtration, dried, and dissolved in DMF (10 ml). HOBt (392 mg, 2.9 mmole), Boc-Arg(Tos)-OH (1.24 g, 2.9 mmole). WSCI (0.53 ml, 2.9 mmole) were added to the above solution while cooling to −15° C. After 16 hours' stirring, water was added to the reaction solution, and the thus-precipitated substance was obtained by filtration and recrystalized two times with methanol to give the object product (3.0 g, 92.9%).

(41) Synthesis of Boc-Arg(Tos)Arg(Tos)Ser(Bzl)Ser(Bzl)Cys(4-MeBzl)-PheGlyGly-OPac A mixture of Boc-Arg(Tos)Ser(Bzl)Ser(Bzl)Cys(4-MeBzl)PheGlyGly-OPac (2.9 g, 2.1 mmole) and TFA (10 ml) was stirred for 50 minutes. TFA was distilled off, and to the residue, 3.5 N HCl in dioxane (0.9 ml, 3.15 mmole) was added. After enough stirring, ether was added. The thus-precipitated solid was obtained by filtration, dried, and then dissolved in DMF (15 ml). HOBt (338 mg, 2.5 mmole), Boc-Arg(Tos)-OH (1.07 g, 2.5 mmole). WSCI (0.46 ml, 2.5 mmole) were added thereto while cooling to −15° C. After 16 hours' stirring, water was added to the reaction solution, and the thus-produced precipitate was obtained by filtration and then treated twice with methanol to obtain the object product (3.1 g, 88.6%).

(42) Synthesis of Boc-LeuArg(Tos)Arg(Tos)Ser (Bzl) Ser(Bzl)Cys(4-MeBzl)PheGlyGly-OPac A mixture of Boc-Arg(Tos)Arg(Tos)Ser(Bzl)Ser(Bzl)Cys(4-MeBzl)PheGlyGly-OPac (3 g, 1.79 mmole) and TFA (10 ml) was stirred for 50 minutes. TFA was dissolved off, and to the thus-obtained residue, 3.5 N HCl in dioxane (0.77 ml, 2.69 mmole) was added. After enough stirring, ether was added. The thus-produced precipitate was obtained by filtration, dried, and dissolved in DMF 15 ml . HOBt (290 mg, 2.15 mmole) and Boc-Leu-OH.$H_2O$ (535 mg, 2.15 mmole), the solution as produced by flashing with $CHCl_3$-toluene Boc-Leu-OH.$H_2O$ (535 mg, 2.15 mmole) and dissolving thus-obtained oily substance in DMF (3 ml), and WSCI (10.39 ml, 2.15 mmole) were added to the solution while cooling to −15° C. After 16 hours' stirring, water was added thereto, and the thus-produced precipitate was obtained by filtration and recrystalized two times with methanol to yield 2.5 g (92.2%).

(43) Synthesis of Boc-Ser(Bzl)LeuArg(Tos)Arg(Tos)Ser(Bzl)Ser(Bzl)Cys(4-MeBzl)PheGlyGly-OPac A mixture of Boc-LeuArg(Tos)Arg(Tos)Ser(Bzl)Ser(Bzl)Cys(4-MeBzl)PheGlyGly-OPac (2.9 g, 1.62 mmole) with TFA (10 ml) was stirred for 50 minutes. TFA was distilled off, and to the residue, 3.5 N HCl in dioxane (0.7 ml, 2.43 mmole) was added and stirred well. The precipitate produced by the addition of ether to the solution was obtained by filtration, dried, and dissolved in DMF (15 ml). HOBt (243 mg, 1.8 mmole), Boc-Ser(Bzl)-OH (531 mg, 1.8 mmole), and WSCI (0.33 ml, 1.8 mmole) were added to the above DMF solution while cooling to $-15°$ C. After 16 hours' stirring, water was added to the reaction solution. The thus-precipitated substance was obtained by filtration and refluxed two times with methanol to obtain the object product (2.94 g, 91.8%).

(44) Synthesis of Boc-Ser(Bzl)LeuArg(Tos)Arg(Tos)Ser(Bzl)Ser(Bzl)Cys(4-MeBzl)PheGlyGly-OH Boc-Ser(Bzl)LeuArg(Tos)Arg(Tos)Ser(Bzl)Ser(Bzl)Cys(4-MeBzl)PheGlyGly-OPac (2.8 g, 1.42 mmole) was dissolved in acetic acid (80 ml) while heating. Powdered zinc (4 g) was added thereto, and the mixture was stirred for 1 hour at 45° C. Zinc was removed by filtration, and the acetic acid was distilled off. To the resulting residue, water was added. The thus-produced precipitate was obtained by filtration, washed with methanol, and then reprecipitated with DMF-MeOH to give the object product, yielding 21.6 g (82.1%).

Amino acid analysis [hydrolysis with 6N HCl]:
Arg: 0.91×2, Ser: 0.89×3, Gly: 1.00×2, Leu: 1.00, Phe: 1.00, ½(Cys)$_2$ :small peak.

Synthesis of protected (Nle$^{12}$)hANP(1-28)

(45) Synthesis of Boc-Arg(Tos)NleAsp(OBzl)Arg(Tos)-IleGlyAlaGlnSer(Bzl)GlyLeuGlyCys(4-MeBzl)-AsnSer(Bzl)PheArg(Tos)Tyr(OBzl)-OBzl The peptide as produced above in (33) (1.88 g, 0.9 mmole) was reacted with TFA (10 ml) for 10 minutes while cooling and for 50 minutes at room temperature, and then 3.5N HCl in dioxane (0.34 ml, 1.08 mmole) was added thereto. The solvent was distilled off, and to the thus-obtained residue, ether was added. The thus-produced precipitate was obtained by filtration and dried overnight on NaOH. The precipitate, together with the carboxylic acid constituent in (39) (1.16 g, 0.95 mmole) and HOBt (1.34 mg, 0.99 mmole), was dissolved in a mixture of NMP (15 ml) with DMP (12 ml). WSCI (180 μl, 0.99 mmole) was added thereto while cooling (pH=5.5) to allow reaction. After 2.5 hours, it gelled. After the substance was stirred overnight, the fluorescamine test was negative. Water was added thereto while cooling, and the thus-produced crystalline substance was obtained by filtration, washed with water and n-hexane, and then dried on P$_2$O$_5$. It was dissolved repeatedly with heated DMF (total volume: 200 ml) and filtered; thereby impurities were removed. DMF was distilled off, and the resulting residue was treated with heated DMF/MeOH to make a gel-like powder of the object product (2.69 g, 93.4%).

Amino acid analysis [6N HCl/PhOH, 108° C., 25 hours]:
Arg: 0.91×3, Asp: 0.99 ×2, Ser: 0.89 ×2, Glu: 0.97, Gly: 1.00 ×3, Ala: 1.00, Cys: small peak, Ile: 1.02, Leu: 1.08, Nle: 1.05, Tyr: 1.00, Phe: 0.96

Elementary analysis: Found: C, 57.53%, H, 6.38%, N, 12.58% Calculation: C, 57.81%, H, 6.27%, N, 12.70%.

(46) Synthesis of Boc-Ser(Bzl)LeuArg(Tos)Arg(Tos)Ser(Bzl)Ser(Bzl)Cys(4-MeBzl)PheGlyGlyArg(Tos)NleAsp(OBzl)Arg(Tos)IleGlyAlaGlnSer(Bzl)GlyLeuGlyCys(4MeBzl)AsnSer(Bzl)PheArg(Tos)Tyr(OBzl)-OBzl:

The peptide as produced above in (45) (1.375 g, 0.43 mmole) was treated with TFA (10 ml) for 10 minutes while cooling and for 50 minutes at room temperature, and then 3.5N HCl in dioxane (0.15 ml, 0.52 mmole) was added thereto. The solvent was distilled off, and to the thus obtained residue, ether was added. The thus-produced powder was obtained by filtration and dried overnight on NaOH. The powder, together with the carboxylic acid constituent (836 mg, 0.45 mmole), and HOBt (0.47 mmole), was dissolved in NMP (25 ml). WSCI (87 μl, 0.47 mmole) was added thereto while cooling (pH=5) to allow reaction. After 1.5 hours, it gelled. After the substance was stirred overnight, the fluorescamine test was negative. Water was added thereto while cooling, and the thus-powdered substance was obtained by filtration, washed with water, n-hexane and ether, and then dried on P$_2$O$_5$. It was purified by suspending it in slightly heated DMF and then treating it with MeOH to obtain the object product, yielding 1.97 g (92.9%).

Amino acid analysis [6N HCl/PhOH, 108° C., 25 hours]:
Arg: 0.93 ×5, Asp: 1.00 ×2, Ser: 0.89 ×5, Glu: 1.00, Gly: 1.02 ×5, Ala: 1.04, Cys: medium peak, Ile: 0.91, Leu: 1.03 ×2, Nle: 0.95, Tyr: 0.81, Phe: 1.00 ×2

Elementary analysis: Found: C, 58.00%, H, 6.41%, N, 12.42% Calculation: C, 58.00%, H, 6.31%, N, 12.68% as C$_{240}$H$_{307}$O$_{51}$N$_{45}$S$_7$Cl$_2$ .2H$_2$O.

(47) Synthesis of [Nle$^{12}$]α-ANP(1-28)

The protected peptide as produced above (641 mg, 0.13 mmole) was reacted with HF (8.5 ml) for 60 minutes at a temperature range of $-2°$ to $-1°$ C., in the presence of anisole (1.7 ml), and the excess HF was distilled off. After the thus-obtained residue was dissolved in about 50% AcOH, it was washed three times with ether, then passed through the column of the resin "Dowex 1×2" (AcO−, 50 ml), eluted with 1N AcOH, and then freezedried. This product was oxidized in the same manner as in the method for the above ANP(5-27) to obtain crude powder. This product was purified by chromatography with the column of CM-C (cellulose) an eluting agent 0.05 M (pH5.0 →0.7 M (pH 5.5) NH$_4$OAc, by chromatography with the column of the resin "HP-20" using as an . 27% CH3CN/5% AcOH, and then by eluting agent 0→27% CH$_3$CN/5% AcOH, and then chromatography with the column of the resin "Sephadex LH-20" using as an eluting agent 1% AcOH, to obtain the object product, yielding 83 mg.

Amino acid analysis [hydrolysis with 6N HCl]:
Arg: 1.02 ×2, Asp: 1.00 ×2, Ser: 0.89 ×5, Glu: 0.98, Gly: 0.99 ×5, Ala: 1.00, Cys: 0.76 ×2, Ile: 0.90, Leu: 1.00 ×2, Nle: 0.90, Tyr: 0.86, Phe: 0.98 ×2

Elementary analysis: Found: C, 45.51%, H, 6.88%, N, 17.67% Calculation: C, 45.37%, H, 6.97%, N, 17.91% as $C_{122}H_{194}O_{38}N_{44}S_2 \cdot 4H_2O$.

Example 4

Synthesis of hANP(5-25)

Synthesis of Boc-Cys(4-MeBzl)AsnSer(Bzl)-OBzl

(48) Synthesis of Ser(Bzl)-OBzl·TosOH

Boc-Ser(Bzl) (8.0 g, 27.1 mmole) was dissolved in DMF (30 ml), and Bzl-Br (3.3 ml, 27.6 mmole) and Et₃N (3.84 ml, 27.6 mmole) were added thereto while cooling and stirring. More Et₃N was added to adjust the pH to ~7. On the next day, water was added to the reaction solution, and then extractd with ethyl acetate. The ethyl acetate phase was washed with water, 5% aqueous NaHCO₃, 1N HCl, and water, in order, and dried over MgSO₄. Ethyl acetate was distilled off. The thus-obtained oily substance was dissolved in AcOH (20 ml), and then TosOH·H₂O (7.8 g, 40.6 mmole) was added thereto. After 1 to 5 hours' stirring, AcOH was distilled off. To the resulting residue ether was added. The thus-produced powder was obtained by filtration, washed sufficiently with ether, and then dried over NaOH to give the object product, yielding 11.15 g (90%).

(49) Synthesis of Boc-AsnSer(Bzl)-OBzl

Ser(Bzl)-OBzl·TosOH (11.15 g, 24.4 mmole), Boc-Agn (6.22 g, 26.8 mmole) and HOBt (3.7 g, 26.8 mmole) were dissolved in DMF (30 ml). WSCI (490 ml, 26.8 mmole) was added dropwise thereto while cooling and stirring. After the addition was completed, the pH of the solution was ≃5. After 3 hours, it was confirmed that the fluorescamine test was negative. Water was added to the reaction solution, separating an oily substance, which was obtained by extraction with ethyl acetate. The ethyl acetate layer was washed with water, 5% aqueous NaHCO₃, water, 1N HCl, and water in order, and then dried with MgSO₄ The ethyl acetate was distilled off, and the thus-obtained solid residue was reprecipitated two times with ethyl acetate/n-hexane to give the object product, yielding 11.13 g (91%).

(50) Synthesis of Boc-Cys(4-MeBzl)AsnSer(Bzl)-OBzl:

Boc-AsnSer(Bzl)-OBzl (10.0 g, 20.0 mmole) was reacted with TFA (45 ml, 0.60 mmole) for 10 minutes while cooling and for 50 minutes at room temperature, and then 3.5N HCl in dioxane (7.0 ml, 24.0 mmole) was added thereto. The excess acid was distilled off, and to the residue, ether was added. The thus-precipitated crystalline substance was obtained by filtration, and dried on NaOH. The crystaline substance, Boc-Cys(-4MeBzl) (6.84 g, 21.0 mmole), and HOBt (2.84 g, 21.0 mmole) were dissolved in DMF (30 ml). WSCI (3.85 ml, 1.0 mmole) was added dropwise thereto while cooling and stirring. The solution was adjusted to pH ≃4 by the addition of Et₃N. On the next day, more WSCI (0.37 ml, 2.0 mmole) was added. After two hours, it was confirmed that the fluorescamine test was negative. Water was poured into the solution, and the thus-precipitated solid was obtained by filtration, washed with water and and ether, and then reprecipitated repeatedly two times with CHCl₃-MeOH/AcOEt to give the object product yielding 12.6 g, (89%).

(51) Synthesis of Boc-AlaGlnSer(Bzl)GlyLeuGlyCys (4-MeBzl)AsnSer(Bzl)-OBzl (17−25)

Boc-Cys(4-MeBzl)AsnSer(Bzl)-OBzl (0.885 g, 1.25 mmole) was reacted with TFA (4 ml, 50 mmole) for 10 minutes while cooling and for 50 minutes at room temperature, and then 6.9N HCl in dioxane (0.22 ml, 1.5 mmole) was added thereto. The excess acid was distilled off, and to the resulting residue ether was added. The thus-powdered substance was obtained by filtration and then dried on NaOH. This powder, Boc-AlaGlnSer(Bzl)GlyLeuGly-OH (0.95 g, 1.31 mmole), and HOBt (0.19 g, 1.38 mmole) were dissolved in DMF (30 ml). WSCI (0.252 ml, 1.38 mmole) was added thereto while cooling and stirring (pH ≃6). After two hours, it was confirmed that the fluorescamine test was negative. Water was added, and the thus-precipitated solid was obtained by filtration, washed with water and with ether, and then reprecipitated with DMF/MeOH to give the object product yielding 1.57g (96%).

Amino acid analysis [6N HCl, 110° C., 22 hours]:
NH₃:1.09 ×2, Asp: 0.99, Ser: 0.91 ×2, Glu: 1.01, Gly: 1.00 ×2, Ala: 1.02, Leu: 1.00

(52) Synthesis of Boc-Arg(Tos)MetAsp(OBzl)Arg(Tos)Ile-GlyAlaGlnSer(Bzl)GlyLeuGlyCys(4-MeBzl)AsnSer-(Bzl)-OBzl(11−25)

Boc-AlaGlnSer(Bzl)GlyLeuGlyCys(4-MeBzl)Asn-Ser(Bzl)OBzl (1.47 g, 1.12 mmole) was reacted with TFA (9 ml, 112 mmole) for 10 minutes while cooling and for 50 minutes at room temperature, and then 6.9N HCl in dioxane (0.25 ml, 1.68 mmole) was added thereto. The excess acid was distilled off, and to the resulting residue, ether was added. The thus-precipitated powder was obtained by filtration and dried on NaOH. The powder, Boc-Arg(Tos)MetAsp-(OBzl)Arg(Tos)IleGly-OH (1.47 g, 1.18 mmole) and HOBt (0.17 g, 1.23 mmole) were dissolved in a mixture of DMF 15 ml NMF (5 ml). WSCI (0.226 ml, 1.23 mmole) was added thereto while cooling and stirring (pH ≃5). On the next day, it was confirmed that the fluorescamine test was negative. To the pudding-like reaction product, water was added, and the thus-precipitated solid was obtained by filtration, washed with water and with ether, and then reprecipitated with DMF/MeOH to give the object product, yielding 2.57 g (94%).

Amino acid analysis [6N HCl, 110° C., 22 hours]:
NH₃:1.13 ×2, Arg: 0.89, Asp: 1:00 ×2, Ser: 0.90 ×2, Glu: 1.04, Gly: 1.01 ×3, Ala: 1.01, Met: 0.39, Ile: 0.93, Leu: 1.00

(53) Synthesis of Boc-Ser(Bzl)Ser(Bzl)Cys(4-MeBzl)Phe-GlyGlyArg-(Tos)MetAsp(OBzl)Arg(Tos)IleGlyAlaGln-Ser(Bzl)-GlyLeuGlyCys(4

(5-25)

Boc-Arg(Tos)MetAsp(OBzl)Arg(Tos)Ile-GlyAlaGln-Ser(Bzl)GlyLeuGlyCys(4-MeBzl)Asn-Ser(Bzl)-OBzl (2.43 g, 1.0 mmole) was reacted with TFA (12 ml) for 10 minutes while cooling and for 50 minutes at room temperature, and then 6.9N HCl in dioxane (0.22 ml, 1.5 mmole) was added thereto. The excess acid was distilled off. Ether was added to the residue produced above to produce a powder, and the powder was dried on NaOH. This powder, together with Boc-Ser(Bzl)Ser(Bzl)Cys(4-MeBzl)PheGlyGly- OH (0.99 g, 1.05 mmole) and HOBt (0.15 g, 1.10 mmole) was dissolved in a mixture of DMF (5 ml) and NMP (20 ml). WSCI (0.201 ml, 1.10 mmole) was added thereto while cooling and stirring (pH: 5 to 6). After 4 hours, it was confirmed that the fluorescamine test was negative. To the pudding-like reaction product, water was added, and the thus-precipitated solid was obtained by filtration, washed with water, n-hexane, and ether, in order, and then reprecipitated with DMF/MeOH to give the object product, yielding 3.0 g (92%).

Amino Acid analysis [6N HCl, 110° C., 22 hours]: $NH_3$:1.26 ×2, Arg: 0.93 ×2, Asp: 1.01 ×2, Ser: 0.92 ×4, Glu: 1.03, Gly: 1.00 ×5, Ala: 1.00, $\frac{1}{2}Ca(Cys)_2$: small peak, Met: small peak, Ile: 0.98, Leu: 1.08, Phe: 0.96

(54) Synthesis of α-hANP(5—25)

The protected peptide as produced above (1.0 g, 0.307 mmole) was treated with TFA (5 ml) for 10 minutes at 0° C. and for 50 minutes at room temperature, and then 6.9N HCl in dioxane (0.1 ml, 0.76 mmole) was added thereto. The excess acid was distilled off, and to the thus-produced residue ether was added to make a powder. The powder was obtained and dried on NaOH. This powder was treated with HF (about 9 ml) in the presence of anisole (1.5 ml, 13.8 mmole) for 1 hour at 0° C. HF was distilled off, and the oily residue was dissolved in 2N AcOH and washed with ether. The water layer was passed through the column with the resin "Dowex 1 ×2" (AcO$^-$, 100 ml) and eluted with 1N HCl. The fraction $S_2$, whose solution had shown positive in the fluorescamine test, were collected, combined together, and freeze-dried.

The freeze-dried substance described above was dissolved in 1N AcOH/urea, and the solution was added dropwise to 1M AcONH$_4$ (pH 7.4)/ 8M urea (270 ml) involving $K_3Fe(CN)_6$ (0.142 g, 0.43 mmole) over 10 minutes. In this addition, the solution was kept at a pH of 7.4 by dropping 10% aqueous ammonia.

After that, the solution was stirred for 10 minutes, and the pH was adjusted to 5 by adding acetic acid. The resin "IRA-45" (Cl$^{31}$, about 20 ml) was added thereto and then stirred slowly for 10 minutes. This solution was passed through the column with the resin "IRA-45" (Cl$^{31}$, 100 ml) and then through the column with the resin "HP—20" (fine, 150 ml), and the two columns were washed with 1N AcOH (600 ml). The column of the resin "HP—20" was eluted with CH$_3$CN/AcOH/-H$_2$O(8:1:1) (500 ml). The thus-eluted solution was concentrated, and the thus-obtained oily residue was freeze-dried with 1N AcOH.

This freeze-dried substance, was dissolved in TFA (30 ml), and NH$_4$I (95 mg, 0.61 mmole)/H$_2$O (1 ml) was added thereto while cooling and stirring. After 10 minutes, water (400 ml) was added to the solution, and the thus-obtained solution was washed with CCl$_4$. To the water layer, ascorbic acid (55 mg) was added, and then the thus-obtained solution was passed through the column with the resin "HP-20" (fine, 100 ml). The column was washed with 1N AcOH (500 ml) and then eluted with CH$_3$CN/AcOH/H$_2$O (8:1:1) (400 ml). The thus-obtained eluents were combined together and concentrated. The resulting oily residue was dissolved in 1N AcOH, and this solution was passed through the column with the resin "Dowex 1 ×2" (AcO$^-$, 100 ml). The column was eluted with 1N AcOH. The fractions whose solution had shown positive in the fluorescamine test were collected, combined together, and freeze-dried.

Next, it was purified by linear gradient elution in the column of CM-cellulose (φ2.65 ×40 cm) : 0.03 M AcONH$_4$ (pH 4.8), 900 ml →0.3M AcONH$_4$ (pH 4.8) (900 ml).

Further, it was eluted by the linear gradient in the column of the resin "HP-20" (φ1.9 ×50 cm) : 0% CH$_3$CN/1%AcOH (600 ml) →20% CH$_3$CN/1% AcOH (600 ml), and the mixture of the object fractions was concentrated and freeze-dried with 1N AcOH. The freeze-dried substance was purified by further elution with the resin "LH-20" column (φ2.13 ×46 cm) using as an eluting agent 1N AcOH.

According to the purification system described above, the purified object product yielded 75 mg (10.3%).

Elementary analysis:
Found C: 42.57%, H 6.54%, N 16.81%
Calculation C: 42.43%, H 6.83%, N 17.09% as $C_{82}H_{133}N_{29}O_{30}S_3 \cdot 12H_2O$ Amino acid analysis [6N HCl, 110° C., 22 hours]:
$NH_3$:2.20 ×2, Arg:0.94 ×2, Asp:1.00 ×2, Ser:0.74 ×4, Glu: 103, Gly:0.99 ×5, Ala:1.02, $\frac{1}{2}(Cys)_2$:0.40 ×2, Met: small peak, Ile:0.91, Leu:0.96, Phe:096

Example 5

Synthesis of α-hANP (7—28)

(55) Synthesis of Boc-Cys(4-MeBzl)PheGlyGly-OH

Boc-Cys(4-MeBzl)PheGlyGly-OPac (3.2g, 4.5 mmole) was dissolved in actic acid (50 ml), and powdered zinc (8g) was added thereto. The mixture was stirred for 50 minutes at 45° C. The zinc was removed by filtration, and then acetic acid was distilled off. To the resulting residue water was added, and the thus-produced precipitate was obtained by filtration, dried, and reprecipitated with methanol/ether to give the object product, yielding 2.27 g (87.3%).

(56) Synthesis of protected α-hANP (7-28)

Synthesis of
Boc-Cys(4-MeBzl)PheGlyGlyArg(Tos)MetAsp(OBzl)Arg(Tos)IleGlyAlaGlnSer(Bzl)GlyLeuGlyCys(4-MeBzl)AsnSer(OBzl)PheArg (2Bzl)-OBzl Boc-Arg(Tos)MetAsp(OBzl)Arg(Tos)IleGlyAlaGlnSer(Bzl)GlyLeuGlyCys(4-MeBzl)AsnSer(Bzl)PheArg(Tos)Tyr (Cl$_2$Bzl)-OBzl (2.09 g, 0.65 mmole) was mixed with TFA (15 ml), and the mixture was stirred for 50 minutes. TFA was distilled off, and to the residue, 3.5 N HCl in dioxane (0.28 ml, 0.98 mmole was added and stirred well. Ether was added thereto. The thus-produced precipitate was obtained by filtration, dried, and then dissolved in NMP (25 ml). HoBt (97 mg 0.72 mmole), Boc-Cys(4-MeBzl)PheGlyGly-OH (422 mg, 0.72 mmole). WSCI (140 μl, 0.72 mmole were added, to the solution while cooling to −15° C. After 16 hours stirring, water was added to the gelled reaction solution, and the thus-precipitated substance was obtained by filtration, washed with MeOH, and then refluxed with MeOH to give the object product, yielding 2.2 g (91.6%).

(57)
Synthesis of CysPheGlyGlyArgMetAspArgIleGly
AlaGlnSerGlyLeuGlyCysAsnSerPheArgTyr (α-hANP-(7-28)]:

To Boc-Cys(4-MeBzl)PheGlyGlyArg(Tos)MetAsp-(OBzl)Arg(Tos)IleGlyAlaGlnSer(Bzl)GlyLeu-GlyCys(4-MeBzl)AsnSer(Bzl)PheArg(Tos)-Tyr(C12Bzl)-OBzl(1 g, 0.27 mmole), TFA (5 ml) was added, and the mixture was stirred for 50 minutes. TFA was distilled off, and to the thus-obtained residue, ether was added. The thus-precipitated substance was obtained by filtration, dried, and then treated with anisole (2 ml) and HF (20 ml) for 60 minutes at 0° C. HF was distilled off, and to the residue, ether was added. The thus-precipitated substance was washed with ether, dissolved in 20% acetic acid, and then passed through the column of the resin "Dowex 1 ×2" (AcO⁻). It was eluted with 1N AcOH. The eluents were collected, combined together and freeze-dried. All the thus-obtained powder was dissolved in 1N AcOH (27 ml), and the solution was added dropwise to the mixture of 1M AcONH₄/urea solution (243 ml) and K₃Fe(CN)₆ (125 mg). In the above case, the solution was adjusted to pH 4 with 10% NH₄OH. In 30 minutes, the dropping was ended, and the solution was adjusted to PH 4.75 with conc. AcOH, mixed with the resin "IRA-45" (Cl-20 ml), and then stirred slowly. Next, the solution was passed through the column with the resin "IRA-45" (Cl-,100 ml) and washed with 1N AcOH. The washings were treated with the resin "HP-20" to adsorb it, and then it was washed with 1% AcOH. It was eluted with CH₃CN/AcOH / water (8:1:1), and the thus-obtained eluent was freeze-dried. The freeze-dried powder was purified by the gradient elution with the CM-cellulose column as an eluting agent 0.05M →0.5M NH₄O Ac. The main fractions (fractions 60 to 67) were collected and freeze-dried. Next, the product was purified with the column of the resin "HP-20" (5% CHCN →25% CH₃CN). The main fractions (fractions 70 to 82) were collected and freeze-dried. In the end, the product was again purified with the resin "LH-20"-column and 2M AcOH to give the purified object product, yielding 78 mg.

Amino Acid analysis [hydrolysis with 6N Hcl]:
Arg:0.98 ×3, Asp:0.99 ×2, Ser:086 ×2,
Glu:1.00, Gly:0.98 ×5, Ala: 109 ½(Cys)₂:0.84 ×2, Met:0.71, Ile:0.93, Leu:1.00, Tyr:0.9, Phe:0.99 ×2
HPLC [Column:Nucleosil 5C₁₈; 0.1% TFA (1%→60% gradient)]
Single peak (26.0 minutes)

Example 6

Synthesis of Asu⁷,²³)α-hANP (7-23)

(58) Synthesis of Boc-AlaGlnSer(Bzl)GlnLeuGlyAsu (OPac)-OBzl

Boc-AlaGlnSer(Bzl)GlyLeuGly-OH (1.23 g, 1.7 mmole), p-TosOH.Asu(OPac)-OBzl (1.03 g, 1.8 mmole) and HOBt (0.26 g, 1.9 mmole) was dissolved in DMF (10 ml). WSCI (0.35 ml, 1.9 mmole) was added thereto at −5° C. The solution was stirred for 1 hour at −5° C and then overnight at room temperature. The reaction solution was poured into cooled water (100 ml), and the thus-precipitated solid was obtained by filtration, washed with water and with ether, and then reprecipitated with chloroform - methanol/ether to give the object product, yielding 1.65 g (88%).

Amino acid analysis [6N HCl - phenol/110° C., 22 hours]:
NH₃:1.08, Ser:0.92, Glu:0.98, Gly:1.03 ×2, Ala:1.00, Asu:1.03, Leu:1.0

Retention time in high speed liquid chromatography of the product: 4.5 minutes. Resin used: Nucleosil 5C₁₈.

Note: Nucleosil 5C₁₈ was used for HPLC unless an exception is noted.
Eluting agent: MeOH-H₂O-TFA (80-20-0.1)
Eluting method: Isocratic

(59) Synthesis of Boc-Arg(Tos)MetAsp(OBzl)Arg(Tos)IleGlyAlaGlnSer(Bzl)GlyLeuGlyAsu(OPac)-OBzl To Boc-AlaGlnSer(Bzl)GlyLeuGlyAsu(OPac)-OBzl (1.5 g, 1.36 mmole), TFA (10 ml was added, and the mixture stirred for 10 minutes at −5° C. and then for 30 minutes at room temperature. The excess TFA was distilled off under reduced pressure, and to the resulting residue, 3.5N HCl in dioxane (0.5 ml) was added to change the free amino group to hydrochloride. Ether was added to the solution, and the thus-precipitated solid was obtained by filtration and dried under reduced pressure for 5 hours over NaOH. This solid was dissolved in DMF (15 ml), and BOC-Arg(Tos)MetAsp-(OBzl)Arg(Tos)IleGly-OH (1.78 g, 1.43 mmole) and HOBt (0.20 g, 1.5 mmole) were added thereto. WSCI (0.28 ml, 1.5 mmole) was added thereto at −5° C. The solution was stirred for 1 hour at −5° C. and then overnight at room temperature. The reaction solution was then poured into cooled water (200 ml). The thus-precipitated solid was obtained by filtration, washed with water and with ether, and reprecipitated with DMF/MeOH to give the object product, yielding 2.6 g (86%).

Amino Acid analysis [6N HCl-phenol, 110° C., 22 hours]:
NH₃:1.13, Arg:0.96 ×2, Asp:1.00, Ser:0.91, Glu:1.00, Gly:1.02 ×3 Ala:0.98, Met:0.62, Asu:1.02, Ile:1.01, Leu:1.08

HPLC Retention time: 12 minutes 45 seconds
Eluting agent : MeOH-H₂O- TFA (80-20-0.1
Eluting method : Isocratic

(60) Synthesis of Boc-PheGlyGly-OH

Boc-PheGlyGly-OPac (2.5 g, 5 mmole) was dissolved in acetic acid (50 ml), and powdered zinc was added thereto. The mixture was stirred for 40 minutes at 45° C. The zinc was removed by filtration, and the solution was concentrated by distillation of the acetic acid. To the resulting residue, water was added, and the thus-precipitated oily substance was obtained by extraction with ethyl acetate. The ethyl acetate layer was washed with 1N HCl and water, and then dried with Na₂SO₄. The ethyl acetate was distilled off. The resulting residue was recrystalized with ethyl acetate-n-hexane to give the object product, yielding 1.75 g (92.1%).

(61) Synthesis of Boc-PheGlyGlyaAg(Tos)MetAsp(OBzl)Arg(Tos)Ile-GlyAlaGlnSer(Bzl)GlyLeuGlyAsu (OPac)-OBzl To Boc-Arg(Tos)MetAsp(OBzl)Arg(Tos)Ile-GlyAlaGln-Ser(Bzl)GlyLeuGlyAsu(OPac)-OBzl (2.2 g, 1 mmole), TFA (10 ml) was added, and the mixture was stirred for 20 minutes at −5° C. and for 30 minutes at room temperature. The excess TFA was distilled off under reduced pressure, and to the residue, 3.5 N HCl in dioxane (0.4 ml) was added to change the free amino group to hydrochloride. Ether was added thereto, and the thus-precipitated solid was obtained by filtration, dried under reduced pressure for 5 hours over NaOH, and dissolved in DMF (30 ml). Boc-PheGlyGly-OH (0.42 g, 1.1 mmole) and HoBt (0.15 g, 1.1 mmole) were added thereto, and WSCI ( 0.20 ml, 1.1 mmole) was added at −5° C. The solution was stirred for 1 hour at −5° C. and overnight at room temperature. The solution obtained by dissolving Boc-PheGlyGly-OH (38 mg, 0.1 mmole) and HOBt (14 mg, 0.1 mmole) in DMF (5 ml) was added to the reaction solution, and WSCI 19 μl, 0.1 mmole) was added thereto at −5° C. The thus-obtained reaction solution was stirred for 1 hour at −5° C. and for 3 hours at room temperature, and then was poured into the cooled 2.5% aqueous sodium bicarbonate (300 ml). The thus-produced precipitate solid was obtained by filtration, washed with water and with ether, refluxed with MeOH (200 ml), cooled naturally, and obtained by filtration to give the object product yielding 2.3.g (92%).

Amino Acid analysis [6N HCl-phenol/110° C. 22 hours]

$NH_3$ 1.07, Arg:0.93×2, Asp:1.00, Ser:0.87, Glu:0.99, Gly:1.03×5, Ala:1.04, Met:0.51, Asu:0.99, Ile:0.97, Leu:1.04, Phe:0.94

HPLC

Retention time: 9 minutes 40 seconds,
Eluting agent: MeOH/$H_2O$/TFA(82.1/27.5/0.1)
Eluting method: isocratic

(62) Synthesis of Boc-PheGlyGlyArg(Tos)MetAsp(OBzl)Arg(Tos)Ile-GlyAlaGlnSer(Bzl)GlyLeuGly-Asu(OH)-OBzl Boc-PheGlyGlyArg(Tos)MetAsp(OBzl)Arg(Tos)Ile-GlyAlaGlnSer(Bzl)GlyLeuGlyAsu(OPac)-OBzl (1.7 g, 0.7 mmole) was dissolved in AcOH-TFE (80 ml - 20 ml), and powdered zinc (2.3 g, 35 mmole) was added thereto. The solution was stirred for 50 minutes at 49° C. An unreacted substance (Pac-derivative) was detected in the solution, so more powdered zinc (2.5 g, 38 mmole) was added. The solution was stirred for 20 minutes at 49° C. Additional powdered zinc (1 g, 15 mmole) was added, and the solution was stirred for 10 minutes at 49° C. The excess zinc was removed by filtration, and the resulting filtrate means concentrated under reduced pressure. Water was added to the residue, and the thus-precipitated solid was obtained by filtration, washed with water and with ether, refluxed with methanol (100 ml), and cooled naturally to give the object product.

Amino acid analysis [6N Hcl-phenol, 110° C., 22 hours]:

$NH_3$:1.10 ×2, Arg:0.95 ×2, Asp:1.00, Ser:0.85, Glu:0.99, Gly:1.02 ×5, Ala:1.05, Met:0.71, Asu:0.99, Ile:0.99, Leu:1.07, Phe:0.98

HPLC

Retention time of HPLC: 5 minutes, 30 seconds
Eluting agent: MeOH-$H_2O$ - TFA (82.5−17.5−0.1)
Eluting method: Isocratic The compound obtained by changing Met to Met(O) is much involved in the product (about 30%). By the way, the retention time of the product in HPLC (with the same conditions as above) was 4 minutes.

(63)

Synthesis of PheGlyGlyArg(Tos)MetAsp(OBzl)—
Arg(Tos)IleGlyAlaGlnSer(Bzl)GlyLeuGlyAsu—OBzl:

To Boc-PheGlyGlyArg(Tos)MetAsp(OBzl)Arg-(Tos)IleGlyAlaGlnSer(Bzl)GlyLeuGlyAsu(OH)-OBzl (0.67 g, 0.28 mmole), TFA (5 ml) was added, and the mixture was stirred for 10 minutes at −5° C. and for 50 minutes at room temperature. The excess TFA was distilled off under reduced pressure, and to the thus-obtained residue, ether was added. The thus-precipitated solid was obtained by filtration, dried under reduced pressure for 2 hours on NaOH, and dissolved in DMF (10 ml). $Et_3N$ (40 μl, 0.28 mmole) was added to this solution at −5° C., the solution was neutralized, and water was added. The thus-precipitated solid was obtained by filtration, washed with water and with ether, and dried under reduced pressure for 2 days on $P_2O_5$. Boc-removed derivative as obtained above was dissolved in DMF (40 ml), HOBt (57 mg, 0.82 mmole) was added thereto, and WSCI.HCl (81 mg, 0.42 mmole) was added at −5° C. The solution was stirred for 1 hour at −5° C. and for 4 hours at room temperature. HOBt (57 mg, 0.42 mmole) and WSCI. HCl (81 mg, 0.42 mmole) were added thereto at −5° C., and the solution was stirred for 1 hour at −5° C. and overnight at room temperature. DMF was distilled off under reduced pressure, and water was added to the residue. The thus-precipitated solid was obtained by filtration, washed with water and with ether, and reprecipitated with MeOH/AcOEt - ether to the object product, yielding 430 mg (68%)

HPLC

Retention time of HPLC: 19 minutes, 50 seconds
Eluting agent: MeOH-$H_2O$- TFA (70-30-0.1) (called "A")

MeOH-$H_2O$- TFA (95−5−0.1) (called "B") Eluting method:

After linear gradient elution with A and B for 15 minutes, the solution was eluted with B for 15 minutes.

Under the same conditions as above, the Met(0) derivative required 17 minutes, 50 seconds, and the de-Boc derivative took 13 minutes, 40 seconds.

(64)

Synthesis of PheGlyGlyArgAspMetArgIleGlyAla—
GlnSerGlyLeuGlyAsu—OH:

A mixture of

PheGlyGlyArg(Tos)Asp(OBzl)MetArg—
(Tos)IleGlyAlaGlnSer(Bzl)GlyLeuGlyAsu—OBzl (338 mg, 0.15 mmole) and HF (5 ml) was stirred in the presence of anisole (0.3 ml) and methionine (34 mg) for 1 hour in the cooling bath. The excess was distilled off under reducecd pressure, and the resulting residue was dissolved in 50% AcOH (5 ml) and then passed through the column with the resin "Dowex 1 ×2" ($AcO^-$, 50 ml). The thus-obtained eluent was concentrated under reduced pressure, and the residue was dissolved in 2M AcOH and freeze-dried to give a crude product. The crude product as obtained above was purified by chromatography with CM-C [Column size: 1.75 ×29 cm;

Eluting solvent: 0.01 M $AcONH_4$ pH 4.8) (called "Abuffer"), 0.4M $AcONH_4$(pH 4.8) (called "B-buffer");

Eluting method: linear gradient elution with A-buffer (300 ml) and B-buffer (300 ml)]to give the product, yielding 90 mg.

The product (40 mg), which was partially purified in the procedure described above, was purified as follows: First, it was dissolved in TFA (2 ml), and 4% aqueous NH$_4$I (110 μl, 30 μmole) was added. The solution was stirred for 10 minutes. Second, an excess of water was added to the reaction solution, and the solution was washed with CCl$_4$. The separated water layer was treated with the resin "Dia-ion HP-20" to adsorb it. The resin was washed with water and treated with CH$_3$CN-10% AcOH for desorption. The thus-obtained element was concentrated under reduced pressure, and the resulting residue was dissolved in 2M AcOH and then passed through the column with the resin "Dowex 1 ×2" (AcO$^-$). The thus-obtained eluent was freeze-dried. The product as obtained above was further purified by column chromatography with the resin "Dia-ion HP-20." [Column size: 1.75×29 cm, Eluting solvent: 10% AcOH (called "A solution"), CH$_3$CN-10% AcOH (25-75) (called "B solution"); Eluting method: linear gradient elution with A solution (300 ml) and B solution (300 ml)].

The fractions involving the object product were collected, combined together, and concentrated. The resulting residue was dissovled in 2M AcOH and freeze-dried. The freeze-dried product was further purified by column chromatogoraphy with the resin "Sephadex LH-20" [Column size: 1.75 ×29 cm; Eluting solvent' 2M AcOH]to give the object product, yielding 21 mg and showing a specific rotation of [α]$_D^{30}$-32.0 (C 0.52 M, AcOH).

Amino acid analysis [6N HCl, 110° C, 22 hours]:

NH$_3$:1.33 ×2, Arg:0.95 ×2, Asp:0.98, Ser:0.92, Glu:0.98, Gly:1.00 ×5, Ala:1.00, Met:0.43, Asu:0.98, Ile:0.97 Leu:1.02, Phe:0.95

HPLC

Retention time of HPLC: 26 minutes

Eluting agent: CH$_3$CN-H$_2$O-TFA(1-99-0.1) (called "A") CH$_3$CN-H$_2$O-TFA(60-40-0.1) (called "B")

Eluting method: linear gradient elution for 25 minutes with A and B, and then for 10 minutes with B.

(65) Synthesis of (Nle$^{12}$) -α-hANP(7-28)

Synthesis of Protected (Nle12) -α-hANP(7-28)

To Boc-Arg(Tos)NleAsp(OBzl)Arg(Tos)Ile-GlyAlaGlnSer(Bzl)GlyLeuGlyCys(4-MeBzl)Asn-Ser(Bzl)PheArg(Tos)Tyr(Cl2Bzl)-(OBzl) (650 mg, 0.20 mmole), TFA (5 ml) was added, and the mixture was stirred for 50 minutes. TFA was distilled off, and to the residue, 3.5 N HCl in dioxane (100 μl, 0.35 mmole) was added and mixed well. Ether was added thereto. The thus-precipitated substance was obtained by filtration, dried, and dissolved in N-methylpyrolidone (15 ml). HoBt (36 mg, 0.26 mmole), Boc-Cys(4-MeBzl)Phe-GlyGly-OH (153 mg, 0.26 mmole) and WSCI (50 FμH1, 0.27 mmole) were added to this solution while cooling to −15° C. After 16 hours, stirring water was added to the gelled reaction solution. The thus-obtained precipitate was separated by filtration and washed two times with MeOH while heating to give the object product, yielding 700 mg.

Amino acid analysis [Hydrolysis with 6N HCl, 110° C, 22 hours]

Arg:0.99 ×3, Asp:1.00 ×2, Ser:0.90 ×2, Glu:1.00, Gly:0.98 ×5, Ala:1.07, ½(Cys)$_2$:medium peak, Nle:0.93, Ile:0.93, Leu:1.00, Tyr:0.92, Phe:0.98 ×2 .

(66)

Synthesis of CysPheGlyGlyArgNleAspArgIleGlyAlaGln

SerGlyLeuGlyCysAsnSerPheArgTyr [(Nle$^{12}$)-α-hANP(7-28)]:

Protected (Nle$^{12}$) -α-hANP(7-28) (500 mg, 0.136 mmole) was treated with HF (10 ml) in the presence of anisole (1 ml at 0° C for 60 minutes). HF was distilled off, and ether was added to the residue. The thus-precipitated substance was waFvHhed with ether and dissolved in 20% AcOH. The solution was passed through the column with the resin "Dowex 1 ×2" (AcO$^-$), and then eluted with 1N AcOH. The thus-obtained eluents were collected, combined together, and freeze-dried. All the thus-obtained powder was dissolved in 1N AcOH (14 ml), and the solution was added dropwise to the solution produced by mixing 1M AcOHH$_4$/ urea solution (126 ml) with K$_3$Fe(CN)$_6$ (63 mg). In this case, the solution was adjusted to a pH of 7.4 with 10% NH$_4$OH. In 30 minutes the addition of 10% NH$_4$OH was ended, and the pH was adjusted to 4.75 with conc. AcOH. The resin "IRA-45" (Cl$^-$) (15 ml) was added thereto, and the solution was slowly stirred. Next, the solution was passed through the column with the resin "IRA−45" (Cl$^-$) (70 ml) and was washed with 1N AcOH. The washings was treated with the resin "HP−20" for adsorption and washed with 1% AcOH. The solution was eluted with the mixing solvent of CH$_3$CN/AcOH/H$_2$O (8/1/1), and the thusobtained eluent was concentrated and freeze-dried. The freeze-dried crude powder was purified by CM-cellulose column chromatography with linear gradient elution as an eluting solvent 0.5 M (pH 5) →0.5M NH$_4$OAC. The main fractions (fractions 50 to 58) were collected, combined together and freeze-dried. Next, the product was further purified by chromatography with gradient elution of the resin "HP−20" as an eluting solvent 5% CH$_3$CN→25% CH$_3$CN. main fractions (fractions 68 to 81) were collected, combined together, and freezedried. Last, the product was further purified with the resin "LH−20" and 2M AcOH to give the object product, yielding 74 mg.

Amino acid analysis [hydrolysis with 6N HCl]:

Arg:0.99 ×3, Asp:1.00 ×2, Ser:0.93 ×2, Glu:1.00, Gly:1.00 ×5, Ala:1.05, ½(Cys)$_2$:0.86 ×2, Nle:0.94, Ile:0.94, Leu:1.00, Tyr:0.95, Phe:0.99 ×2

Example 7

Synthesis of Met(0)12-α-hANP(1−28)

(67) Synthesis of Boc-Ser(Bzl)LeuArg(Tos)Arg(Tos) Ser(Bzl)SerCys(4-MeBzl)PheGlyGlyArg(Tos)Met Asp(OBzl)Arg(Tos)IleGlyAlaGlnSer(Bzl)GlyLeuGly Cys(4-MeBzl)AsnSer(Bzl)PheArg(Tos) Tyr (Cl$_2$Bzl)-OBzl A mixture of Boc-Arg(Tos)MetAsp(OBzl)Arg(Tos-)IleGlyAlaGlnSer(Bzl)GlyLeuGlyCys(4-MeBzl)Asn-Ser(Bzl)PheArg(Tos)Tyr(Cl$_2$Bzl)-OBzl (2.02g, 0.63 mmole) and TFA (20 ml) was stirred for 50 minutes. TFA was distilled off, and to the resulting residue, 3.5N HCl in dioxane (0.27 ml) was added. The solution was stirred well, and ether was added thereto. The thus-precipitated substance was obtained by filtration, dried, and dissolved in N-methyl pyrolidone (30 ml) . Then, HOBt (89 mg, 0.66 mmole), Boc-Ser(Bzl)Leu(Tos)Arg-(Tos)Arg(Tos)Ser(Bzl)Ser(Bzl)Cys(4-MeBzl)Phe- GlyGly-OH (1.22 g, 0.66 mmole) and WSCI (120 μl, 0.66 mmole) were added thereto under cooling to −15° C. After 16 hours' stirring, water was added to the gelled reaction solution, The thus-precipitated substance was obtained by filtration, washed with methanol, and then refluxed with methanol to give the object product, yielding 3.0 g (96.5%).

Amino acid analysis [hydrolysis with 6N HCl]:
Arg:0.98 ×5, Asp:1.00 ×2, Ser:0.90 ×5, Glu:1.07, Gly: 1.02 ×5, Ala:1.01, ½(Cys)$_2$:0 19, Met:0.60, Ile:0.89, Leu:1.08 ×2, Try:0.97, Phe:1.01 ×2

(68) Synthesis of Met(0)12-o-hANP(1−28):

To Boc-Ser(Bzl)LeuArg(Tos)Arg(Tos)Ser(Bzl)Ser(Bzl)Cys(4-MeBzl)PheGlyGlyArg(Tos)MetAsp(OBzl)Arg(Tos)IleGlyAlaGlnSer(Bzl)GlyLeuGlyCys(4-MeBzl)AsnSer(Bzl)PheArg(Tos)-Tyr(C12Bzl)-OBzl (1 g, 0.2 mmole), TFA (5 ml) was added. The solution was stirred for 50 minutes. TFA was distilled off, and ether was added to the resulting residue. The thus-obtained precipitate was separated by filtration, dried, and reacted with HF (30 ml) in the presence of anisole (1.5 ml) for 60 minutes at 0° C. HF was distilled off. The thusobtained residue was washed well with ether and dissolved in 2N AcOH. The solution was passed through the column with the resin "Dowex 1 ×2" (AcO$^-$), and it was eluted with 1N AcOH. The thus-obtained eluent was concentrated and freeze-dried. This freeze-dried powder was dissolved in 1M acetic acid (20 ml), and the solution was added dropwise to the solution produced by mixing 1M NH$_4$OAc-urea solution (180 ml) with K$_3$Fe(CN)$_6$ (93 mg). In this case, a pH of 7.4 was maintained by adding 10% NH$_4$OH. In 30 minutes, addition of 10% NH$_4$OH was ended. The solution was adjusted to pH 4.75 with AcOH and mixed with the resin "IRA−45" (Cl, 200 ml). The mixture was stirred slowly. The solution was passed through the column with resin "IRA−45" (Cl$^-$, 100 ml). The thus-obtained eluent was passed through the column with the resin "HP−20" for adsorption. It was washed with 1% AcOH and then eluted with CH$_3$CN-H$_2$O-AcOH (8/1/1), and the thus-obtained eluent was concentrated and freeze-dried. The thus-obtained powder was purified by column chromatography with CM-cellulose and gradient elution as an eluting agent 0.05 →0.7M NH$_4$OAc (1 1 →1 1). The main fractions (fractions 89 to 99) were collected, combined, and freeze-dried. The thus-obtained powder was purified by the resin "HP−20" and then by the resin "LH−20." A part of the thus-purified powder (10 mg) was dissolved in 1N AcOH (3 ml), and H$_2$O$_2$ (0.5 ml) was added thereto. The solution was stirred for 20 minutes and then contacted with the resin "HP−20" for adsorption. It was washed with 1% AcOH and eluted with CH$_3$CN-H$_2$OAcOH (8/1/1). The thus-obtained eluent was concentrated and freeze-dried to obtain Met-(O)12 -α- hANP(1−28)yielding 6 mg. ,(1−28);
HPLC [Column:nucleosil 5C$_{18}$:0.1% TFA, CH$_3$CN 1% 60% gradient elution]
Single peak, 24.8 minutes
Amino acid analysis [hydrolysis with 6N HCl]:
Arg:1.00 ×5, Asp:1.00 ×2, Ser:0.91 ×5, Glu:1.01, Gly:1.02 ×5, Ala:1.06, ½(Cys)$_2$:0.82 ×2, Met:0.89, Ile:0.92, Leu:1.05 ×2, Try:0.89, Phe:1.00 ×2

Example 8

Synthesis of [Met12, Asu7,23]-α-hANP(7−28)

1 Synthesis of
Boc-Ala-Gln-Ser(Bzl)Gly-Leu-Gly-Asu(OPac)-Asn-Ser(Bzl)-Phe-Arg(Tos)-Tyr(Cl$_2$Bzl)-OBzl Boc-Asu(OPac)-Asn-Ser(Bzl)-Phe-Arg(Tos)-Tyr(Cl$_2$Bzl)-OBzl (0.95 g, 0.60 mmole) was reacted with CF$_3$CO$_2$H (4 ml, 70 times mole) for 20 minutes while cooling and for 40 minutes at room temperature, and 5.9N HCl in dioxane (0.2 ml, 1.5 times mole) was added thereto. The excess acid was distilled off. To the residue, ether was added and the thus-obtained powder was dried under reduced pressure over NaOH.

This powder, Boc-Ala-Gln-Ser(Bzl)-Gly-Leu-OH (0.455 g, 1.05 times mole), and HOBt (90 mg, 1.1 times mole) were dissolved in a mixed solvent of Nmethylpyrolidone/DMF (2:1). WSCI 0.121 ml, 1.1 times mole) was added dropwise thereto while stirring and cooling to −20° C. pH ≃5. After the solution was stirred overnight, the fluorescamine test was negative. Water was added to the reaction solution, and the thus-precipitated solid material was obtained by filtration and washed with water and then with ether. It was reprecipitated with chloroformmethanol/ether to obtain the desired product, yielding 0.88 g (68%).

Amino acid analysis [hydrolysis with 6N HCl, 110° C, 22 hours' addition of phenol]: NH$_3$1.16 ×2, Arg:0.94, Asp:1.00, Ser:0.90 ×2, Glu:0.98, Gly:0.98 ×2, Ala:1.00, Asu:1.02, Leu:0.98, Tyr:0.91, Phe:0.97

(2) Synthesis of
Boc-Ala-Gln-Ser(Bzl)-Gly-Leu-Gly-Asu(OH)-Asn-Ser(Bzl)-Phe-Arg(Tos)-Tyr(Cl$_2$Bzl)-OBzl Boc-Ala-Gln-Ser(Bzl)-Gly-Leu-Gly-Asu(OPac)-Asn-Ser(Bzl)-Phe-Arg(Tos)-Tyr(Cl$_2$Bzl)-OBzl (0.84 g, 0.387 mmole) was dissolved in CH$_3$COOH (60 ml) and stirred while heating to about 45° C for 1 hour in the presence of zinc-powder.

The catalyst was removed by filtration, and CH$_3$COOH was distilled off. Water was added to the residue and the thus-precipitated solid material was obtained by filtration and washed with water and with ether. It was reprecipitated with chloroformmethanol/ether to give the object product, yielding 0.68 g (86%).

(3) Synthesis of
Boc-Phe-Gly-Gly-Arg(Tos)-Met-Asp(OChx)-Arg(Tos)-Ile-Gly-OPac

Boc-Arg(Tos)-Met-Asp(OChx)-Arg(Tos)-Ile-Gly-OPac (1.35 g, 1.0 mmole) was reacted with CH$_3$CO$_2$H (6 ml, 100 times mole) for 20 minutes while cooling and for 40 minutes at room temperature, and 5.9N HCl/dioxane (0.21 ml, 1.2 times mole) was added thereto. The excess acid was distilled off. Ether was added to the residue and the thus-obtained powder was separated by filtration and dried under reduced pressure over NaOH. This powder, Boc-Phe-Gly-Gly-OH (0.40 g, 1.05 times mole), and HOBt (0.15 g, 1.1 times mole) were dissolved in the mixtured solvent (15 ml) of Nmethylpyrolidone/DMF (1:2). WSCI (0.201 ml, 1.1 times mole) was added thereto while cooling to −20° C and stirring, pH ≃5.

The next day, the fluorescamine test was negative.

The reaction solution was poured into water, and the thus-precipitated solid material was obtained by filtration and washed with water and with ether.

It was reprecipitated with CHCl$_3$-MeOH/ether to give the object product (1.48 g, 92%).

(4) Synthesis of
Boc-Ala-Gln-Ser(Bzl)-Gly-Leu-GlyAsu[Phe-Gly-Gly-Arg(Tos)-Met-Asp(OChx)-Arg(Tos)-Ile-Gly-OPac]-Asn-Ser(Bzl)-Phe-Arg(Tos)-Tyr(C12Bzl)-OBzl Boc-Phe-Gly-Gly-Arg(Tos)-Met-Asp(OChx)-Arg(Tos)Ile-Gly-OPac (0.14 g, 86.5 nole) was reacted with CF$_3$CO$_2$H (1 ml, 100 times mole) for 20 minutes while cooling and for 40 minutes at room temperature, and 5.9 N HCl/dioxane (0.1 ml) was added thereto. The excess acid was distilled off. Ether was added to the residue, and the thus-obtained powder was separated by filtration and dried under reduced pressure on NaOH.

This powder, Boc-Ala-Gln-Ser(Bzl)-Gly-Leu-Gly-Asu-Asn-Ser(Bzl)-Phe-Arg(Tos)-Tyr(Cl$_2$Bzl)-OBzl (0.18 g, 1.05 times mole), and HOBt (15 mg, 1.1 times mole) were dissolved in N-methylpyrolidone/DMF (5:1, 6 ml). WSCI (18 μl, 1.1 times mole) was added thereto while cooling to −20° C and stirring, pH ≃5. On the following day, water was added to the reaction solution and the thus-precipitated solid material was obtained by filtration, washed with water and with ether, and reprecipitated with DMF/ether to give the object product (0.25 g, 81%).

Amino acid analysis:
NH$_3$:1.22 ×2, Arg:0.96 ×3, Asp:1.00 ×2, Ser:0.98 ×2, Glu:1.10, Gly:0.98 ×5, Ala:1.10, Met:0.66, Asu:1.10, Ile:0.89, Leu:1.17, Tyr:1.04, Phe:0.99 ×2

(5) Synthesis of
Boc-Ala-Gln-Ser(Bzl)-Gly-Leu-Gly-Asu[Phe-Gly-Gly-Arg(Tos)-Met-Asp(OChx)-Arg(Tos)-Ile-GlyOH]-Asn-Ser(Bzl)-Phe-Arg(Tos)-Tyr(Cl$_2$Bzl)-OBzl:

Boc-Ala-Gln-Ser(Bzl)-Gly-Leu-Gly-Asu[Phe-Gly-Gly-Arg(Tos)-Met-Asp(OChx)-Arg(Tos)-Ile-Gly-OPac]-AsnSer(Bzl) -Phe-Arg(Tos)-Tyr(Cl$_2$(Bzl)-OBzl (10.22 g, 61.9 FvH mole) was dissolved in CH$_3$CO-FvH1 (10 ml) and stirred for 1 hour in the presence of Zinc-powder (1.0 g) while heating to 45° C. The catalyst was removed by filtration, and CH$_3$CO$_2$H was distilled off. Water was added to the residue, and the thus-precipitated solid was separated by filtration, washed with water and with ether, and reprecipitated with DMF/ether to give the desired product (0.20 g, 95%).

the thus-precipitated powder was obtained by filtration and dried under reduced pressure on NaOH.

This powder and HOBt (15 mg, 2 times mole) were dissolved in DMF (30 ml), and WSCI (11.1 μl, 1.1 mole) was added thereto while cooling to −20° C and stirring, pH ≃5. After 2 hours, WSCI.HCl (11 mg, equi mole) was added. The next day, the fluorescamine test was negative. DMF was distilled off. Water was added to the residue. The thus-precipitated solid was obtained by filtration, washed with water and with ether, and reprecipitated with DMF/ether to give the object product (0.15 g, 82%).

Amino acid analysis:
NH$_3$:1.27, Arg:0.96 ×3, Asp:1.00 ×2, Ser:0.98 ×2, Glu:1.0, Gly:0.97 ×5, Ala:1.11, Met:0.63, Asu:1.12, Ile:0.89, Leu:1.16, Tyr:1.01, Phe:0.99 ×2

(7) Synthesis of deamino Met$^{12,}$ Asu$^{7,23}$]-α-hANP(7-28)

Protected and ring-forming [Met12, Asu7,23]-α-hANP(7−28) (130 mg, 39.1 μmole) was reacted with HF (5 ml) in the presence of anisole (0.4 ml, 80 times mole) for 1 hour while cooling. HF was distilled off, and the residue was dissolved in 50% CH$_3$CO$_2$H. A water layer was washed with ether and passed through the column of the resin "Dowex 1 ×2" (Aco$^-$, 30 ml). It was eluted with 1N CH$_3$CO$_2$H, and the fractions that were positive in the Pauly test were collected, combined together, and freeze-dried. It was further purified as follows:

1. CM-cellulose (φ2.1 ×22 cm) column purification: linear gradient elution of 0.03 M AcONH4 (pH 4.8) →0.3M (each 300 ml) . Yield: 40 mg.
2. "HP−20" (φ2.1 ×23 cm) column purification: linear gradient elution of 0% →30% CHFvHCN/1NAcOH (each 400 ml). Yield' 12 mg (13%).

Amino acid analysis: NH$_3$:1.89 ×2, Arg:0.99 ×3, Asp:0.99 ×2, Ser:0.88 ×2, Glu:0.98, Gly:1.00 ×5, Ala:1.02, Met: small ∼middle peak, Asu:1.05, Ile:1.05, Leu:1.14, Tyr:0.93, Phe:0.99 ×2

Example 9

Synthesis of [Ile$^{12,}$ Asu$^{7,23}$]-α-hANP(7−28)

(1) Synthesis of
Boc-Phe-Gly-Gly-Arg(Tos)-Ile-Asp(OChx)-Arg(Tos)-Ile-Gly-OPac

The object product (0.61 g, 95%) was obtained in the same manner as in Example 8 (1) using as starting materials Boc-Arg(Tos)-Ile-Asp(OCHx)-Arg(Tos)-Ile-GlyOPac (0.535 g, 0.40 mmole) and Boc-Phe-Gly-Gly (0.16 g, 1.05 mole).

(6)

Synthesis of ⌐Phe—Gly—Gly—Arg(Tos)—Met—Asp(OChx)—
—Arg(Tos)—Ile—Gly—Ala—Gln—Ser(Bzl)—Gly—Leu—Gly—Asu—Asn—
—Ser(Bzl)—Phe—Arg(Tos)—Tyr—(Cl$_2$Bzl)—OBzl Boc-Ala-Gln-Ser(Bzl)-Gly-Leu-Gly-Asu[Phe-Gly-Gly-Arg(Tos)-Met-Asp(OChx)-Arg(Tos)-Ile-Gly-OH]-Asn-Ser(Bzl)-Phe-Arg(Tos)-Tyr(Cl$_2$Bzl)-OBzl (0.19 g, 55.3 μmole) was reacted with CF$_3$CO$_2$H (1 ml, 220 times mole) for 10 minutes while cooling and for 50 minutes at room temperature, and 5.9N HCl/dioxane (20 μ,2 times mole) was added thereto. The excess acid was distilled off. Ether was added to the residue, and Amino acid analysis:
Arg:0.98, Asp:1.03, Gly:1.00 ×3, Ile:0.98 ×2, Phe:0.99

(2) Synthesis of
Boc-Ala-Gly-Ser(Bzl)-Gly-Leu-GlyAsu[Phe-Gly-Gly-Arg(Tos)-Ile-Asp(OChx)-Arg(Tos)-Ile-Gly-OPac]-Asn-Ser(Bzl)-Phe-Arg(Tos)-Tyr(Cl$_2$Bzl)-OBzl The object product (0.62 g, 91%) was obtained in the same manner as in Example 8 (4) using as starting materials the peptide as mentioned above (1), (0.31 g, 0.194 mmole) and Boc-Ala-Gln-Ser(Bzl)-Gly-Leu-Gly-Asu(OH)-Asn-Ser(Bzl)-Phe-Arg(Tos)-Tyr(Tos)-OBzl (0.406 gl, 1.02 times mole).

(3) Synthesis of
Boc-Ala-Gln-Ser(Bzl)-Gly-Leu-Gly-Asu[Phe-Gly-Gly-Arg(Tos)-Ile-Asp(OChx)-Arg(Tos)-Ile-GlyOH]-Asn-Ser(Bzl)-Phe-Arg(Tos)-Tyr(Cl$_2$Bzl)-OBzl The object product (0.55 g, 94%) was obtained in the same manner as in Example 8 (5) using as a starting material the peptide as mentioned above (2) (0.60 g, 0.17 mmole).

(4) Synthesis of Phe—Gly—Gly—Arg(Tos)—Ile—Asp(OChx)—
—Arg(Tos)—Ile—Gly—Ala—Gln—Ser(Bzl)—Gly—Leu—Gly—Asu—Asn—
—Ser(Bzl)—Phe—Arg(Tos)—Tyr—(Cl$_2$Bzl)—OBzl:

The object product (0.44 g, 88%) was obtained in the same manner as in Example 8 (4) as a starting material the peptide as mentioned above (3) (0.51 g, 0.15 mmole).
Amino acid analysis:

NH$_3$:1.28 ×2, Arg:0.92 ×3, Asp:1.00 ×2, Ser:0.91 ×2, Glu:1.01, Gly:0.97 ×5, Ala:1.03, Asu:0.96, Ile:0.85 x 2, Leu:0.93, Tyr:0.95, Phe:0.94 ×2

(5) Synthesis of Deamino [Ile$^{12}$, Asu$^{7,23}$]-α-hANP7-28)

The object and purified product (20 mg, 8%) was obtained in the same manner as Example 8 (7) using as a starting material the peptide mentioned above (4) (0.40 g, 0.12 mmole).
Amino acid analysis:
NH$_3$1.23 ×2, Arg:0.97 ×3, Asp:1.00, Ser:0.95 ×2, NH$_3$:1. Glu:0.96, Gly:1.00, Ala:1.02, Asu:1.06, Ile:1.02 ×2, Leu:1.03, Tyr:0.93, Phe:0.97 ×2

Example 10

Synthesis of [Nle12, Asu7,23]-α-hANP7-28)

(1) Synthesis of
Boc-Phe-Gly-Gly-Arg(Tos)-Nle-Asp(OBzl)-Arg(Tos)-Ile-Gly-OPac

The object product (0.37 g, 79%) was obtained in the same manner as in Example 8 (1), using as starting materials Boc-Arg(Tos)-Nle-Asp(OBzl)-Arg(Tos)-Ile-GlyOPac (0.40 g, 0.297 mmole) and Boc-Phe-Gly-Gly (0.117 g, 1.05 mole).

(2) Synthesis of
Boc-Ala-Gln-Ser(Bzl)-Gly-Leu-GlyAsu[Phe-Gly-Gly-Arg(Tos)-Nle-Asp(OBzl)-Arg(Tos)-Ile-Gly-OPac]-Asn-Ser(Bzl)-Phe-Arg(Tos)-Tyr(Cl$_2$Bzl)-OBzl The object product (0.364 g, 85%) was obtained in the same manner as in Example 8(4), using as starting materials the peptide mentioned above (1) (0.195 g, 0.121 mmole) and Boc-Ala-Gln-Ser(Bzl)-Gly-Leu-Gly-Asu(OH)-Ser(Bzl)-Phe-Arg(Tos)-Tyr(Cl$_2$Bzl)-OBzl (0.254 g, 1.02 mmole).
Amino acid analysis:
NH$_3$:1.23 ×2, Arg:0.94 ×3, Asp:1.00 ×2, Ser:0.94 ×2, Glu:1.04, Gly:0.99 ×5,Ala:1.04, Nle:0.96, Asu:1.12, Ile:0.92, Leu:1.11, Tyr:1.02, Phe:0.96 ×2

(3Synthesis of
Boc-Ala-Gln-Ser(Bzl)-Gly-Leu-Gly-Asu[Phe-Gly-Gly-Arg(Tos)-Nle-Asp(OBzl)-Arg(Tos)-Ile-GlyOH]-Asn-Ser(Bzl)-Phe-Arg(Tos)-Tyr(Cl$_2$Bzl)-OBzl The object product (0.29 g, 89%) was obtained in the same manner as in Example 8 (5), using as a starting material the peptide mentioned above (2) (0.34 g, 96 μmole).

(4) Synthesis of Phe—Gly—Gly—Arg(Tos)—Nle—Asp(OBzl)—
—Arg(Tos)—Ile—Gly—Ala—Gln—Ser(Bzl)—Gly—Leu—Gly—Asu—Asn—
—Ser(Bzl)—Phe—Arg(Tos)—Tyr(Cl$_2$Bzl)—OBzl:

The object product (0.22 g, 88%) was obtained in the same manner as in Example 8 (6) using as a starting material the peptide mentioned above (3) (0.26 g, 75.9 μmole).
Amino acid analysis:
NH3:1.3 ×2, Arg:0.94 ×3, Asp:1.00 ×2, Ser:0.94 ×2, Glu:1.05, Gly:0.98 ×5, Ala:1.03, Nle:0.99, Asu:1.16, Ile:0.97, Leu:1.14, Tyr:1.03, Phe:0.96 ×2

(5) Synthesis of Deamino [Nle12, Asu7,23]-o-hANP7-28):

The object and purified product (28 mg, 20%) was obtained in the same manner as Example 8 (7), using as a starting material the peptide mentioned above (4) (0.20 g, 0.060 mmole).
Amino acid analysis:
NH$_3$:1.33 ×2, Arg:1.00 ×3, Asp:1.02 ×2, Ser:0.90 ×2, Glu:0.98, Gly:1.00 ×5, Ala:1.00, Nle:0.99, Asu:1.08, Ile:1.02, Leu:1.03, Tyr:0.95, Phe:0.98 ×2

Example 11

"Synthesis of (Nle12)-α-hANP7-28)

(1) Synthesis of Protected (Nle$^{12}$)-FvH- hANP7-28)

To Boc-Arg(Tos)-Nle-Asp(OBzl)-Arg(Tos)-Ile-Gly-Ala-Gln-Ser(Bzl)-Gly-Leu-Gly-Cys(4CH$_3$Bzl)-Asn-Ser(Bzl)Phe-Arg(Tos)-Tyr(Cl$_2$Bzl)-OBzl (650 ml, 0.20 mmole), TFA (5 ml) was added and stirred for 50 minutes. TFA was distilled off, and to the residue, 3.5N HCl/dioxane (114 FvH1, 0.4 mmole) was added and stirred well. Ether was added thereto. The thus-precipitated solid was obtained by filtration, dried, and dissolved in Nmethylpyrolidone (15 ml). HOBt (36 mg), BocCys(4CH$_3$Bzl)-Phe-Gly-Gly-OH (153 mg), and WSCI (48 FvH1) were added thereto while cooling to −15° C. The solution was stirred for 16 hours, and in the fluorescamine test was negative. To the gelled reaction solution, water was added, and the thusproduced precipitate was obtained by filtration and refluxed twice with methanol to give the object product, yielding 700 mg (95.4%).

Amino acid analysis: NH$_3$:2.02, Arg:0.88 ×3, Asp:1.00 ×2, Ser:0.89 ×2, Glu:1.00, Gly:1.02 ×5, Ala:1.03, ½(Cys) 2:small peak, Nle:0.88, Ile:0.89, Leu:0.97, Tyr:0.87, Phe:1.01 ×2.

(2) Synthesis of (Nle12) -α-hANP(7-28)

The protected (Nle$^{12}$) -α-hANP7-28) (650 mg, 0.177 mmole) was treated with anisole (1 ml) and HF (10 ml) at 0° C for 60 minutes. HF was distilled off, and ether was added to the residue, The thus-produced precipitate was waFvHhed well with ether and dissolved in 1N CH$_3$CO$_2$H. The solution was passed through the column of the resin "Dowex 1 ×2" (AcO$^-$). It was eluted with 1N CH$_3$CO$_2$H. The obtained eluent was dried to produce a powder and dissolved in 1N CH$_3$CO$_2$H (18 ml). This solution was added dropwise to the mixed solution of 1M NH$_4$OAc/6M urea solution (162 ml) and K$_3$Fe(CN)$_6$ (83 mg). In this case, the pH value was kept to 7.4 with 10% NH$_4$OH. After the addition of the NH$_4$OH, the solution was stirred for 30 minutes. It was adjusted to pH 4.75 with CH$_3$CO$_2$H and passed through the column of "IRA−45" (Cl$^-$, 100 ml). It was then washed with CH$_3$CO$_2$H. The washings were desalted with the resin "Diaion HP-20" and eluted with acetonitrile/water/CH$_3$CO$_2$H(8/1/1). The eluent was concentrated and freeze-dried. The thus-obtained powder was purified by the chromatography of CM-cellulose and a gradient elution of 0.05 →0.4M HN$_4$OAc. The fractions 50 to 57 were collected, combined together, and freeze-dried. The obtained powder was further purified by the chromatography of the resin "Diaion HP-20" and a gradient elution (eluting solvent: 5%CH$_3$CN →25%CH$_3$CN/5% CH$_3$CO$_2$H). The fractions 75 to 87 were collected, combined together, and freeze-dried. Next, it was desalted with Sephadex "LH-20". It was eluted with 2N CH$_3$CO$_2$H. The fractions 11 to 15 were collected, combined together, and freeze-dried to obtain the object and purified product, yielding 64 mg.

It showed a single peak at 25.5 minutes by highspeed liquid chromatography with the column of nucleosile 5C$_{18}$, and 1∼60% CH$_3$CN/0.1% TFA as an eluting solution.

Amino acid analysis:
NH$_3$:2.57, Arg:1.03 ×3, Asp:1.01 ×2, Ser:0.91 ×2, Gln:0.99, Gly:1.00 ×5, Ala:1.01, ½(Cys)$_2$:0.86 ×2, Nle:0.93, Ile:0.91, Leu:0.96, Tyr:0.81, Phe:1.00.

Example 12

Synthesis of α-hANP(4- 28)

(1) Synthesis of Boc-Arg(Tos)-Ser(Bzl)-Ser(Bzl)-Cys(4-()CH$_3$Bzl)-Phe-Gly-Gly-OH Boc-Arg(Tos)-Ser(Bzl)-Ser(Bzl)-Cys(4CH$_3$Bzl)-Phe-Gly-Gly-OPac (2g, 1.46 mmole) was dissolved in CH$_3$CO$_2$(100 ml), and zinc-powder (5 g) was added.

The solution was stirred for 50 minutes at 45° C. The zincpowder was removed by filtration, and CH$_3$CO$_2$H was distilled off. To the residue water was added and the thus-produced precipitate was obtained by filtration and then recrystalized with methanol to the object product (1.5 g, 82.0%).

Amino acid analysis:
Arg:0.98, Ser:0.87 ×2, Gly:1.00 ×2, ½(Cys)$_2$:small peak, Phe:1.00

(2) Synthesis of Protected α-hANP(4−28):

Boc-Arg(Tos)-Ser(Bzl)-Ser(Bzl)-Cys(4-CH$_3$Bzl)-Phe-Gly-Gly-Arg(Tos)-Met-Asp(OBzl)-Arg(Tos)-Ile-Gly-Ala-
Gln-Ser(Bzl)-Gly-Leu-Gly-Cys-(4-CH$_3$Bzl)-Asn-Ser(Bzl)Phe-Arg(Tos)-Tyr(Cl$_2$Bzl)-OBzl

Boc-Arg(Tos)-Met-Asp(CHx)-Arg(Tos)-Ile-Ala-Gln-Ser(Bzl)-Gly-Leu-Gly-Cys(4-CH$_3$Bzl)-Asn-Ser(Bzl)-Phe-Arg-Tyr(Cl$_2$Bzl)-OBzl (0.644 g, 0.20 mmole) was treated with CF$_3$CO$_2$H (3 ml) for 10 minutes while cooling to −5° C and for 50 minutes at room temperature, and 5.9N HCl/dioxane (60 μl, 1.5 times mole) was added. The excess acid was distilled off. Ether was added to the residue. The obtained powder was dried over NaOH.

This powder, Boc-Arg(Tos)-Ser(Bzl)-Cys(4CH$_3$Bzl)-Phe-Gly-Gly-OH (0.263 g, 1.05 times mole) and HOBt (30 mg, 1.1 times mole) were dissolved in DMF (4 ml) and Nmethylpyrolidone (4 ml). WSCI (40.3 FvH1, 1.1 mole) was added thereto while cooling to not more than 20° C and stirring. The pH value of the reaction solution was about 6.

On the following day, the fluorescamine test was negative. Water was poured into the precipitated gel. The thus-produced solid was obtained by filtration and washed with water, n-hexane, and ether, in order.

The material was suspended in DMF, and methanol was added thereto. The thus-produced powder was obtained by filtration and washed with methanol to the object product (0.79 g, 91%).

Amino acid analysis:
NH$_3$:1.27 ×2, Arg:0.89 ×4, Asp:1.00 ×2, Ser:0.88 ×4, Glu: 1.09, Gly:1.00 ×5, Ala:1.03, ½(Cys)$_2$:0.18 ×2, Met:0.29, Ile:0.90, Leu:0.98, Tyr:0.96, Phe:0.97 ×2.

(3) Synthesis of -α-hANP(4−28):

The protected peptide α-h-ANP(4−28) (0.61 g, 0.14 mmole) was reacted with CF$_3$CO$_2$H (3 ml) for 10 minutes while cooling to −5° C and for 40 minutes at room temperature, and 5.9N HCl/dioxane 60 μl ) was added thereto. The excess acid was distilled off, and to the residue ether was added. The thus-produced powder was obtained and dried over NaOH.

This powder was treated with anhydrous HF (about 8 ml) in the presence of anisole (1.1 ml) for 1 hour while cooling. HF was distilled off while cooling. The thus-obtained residue was dissolved in 50% CH$_3$CO$_2$H, diluted with water, and washed with ether. The water phase was passed through the column of the resin "Dowex 1 ×2" (AcO$^-$, 40 ml). It was eluted with 1N CH$_3$CO$_2$H. The fractions that were positive in the Pauly test were collected, combined together and freeze-dried.

The freeze-dried product was dissolved in 1N CH$_3$CO$_2$H (20 ml) involving urea. The solution was added dropwise to 1M AcONH$_4$ (pH 7.4)/8M urea (120 ml) involving K$_3$Fe(CN)$_6$ (65 mg, 1.4 mole) over about 10 minutes. Meanwhile, the pH value was kept to 7.4 by the addition of 10% ammonia. The solution was stirred for an additional 10 minutes and then adjusted to pH 4 to 5 with CH$_3$CO$_2$H. The resin "IRA−45" (Cl$^-$, 30 ml) was added thereto and was stirred slowly. Next, the solution was passed through the column of the resin "IRA-45" (Cl$^-$, 30 ml) and then that of the resin "HP-20" (fine, 50 ml), It was washed with CH$_3$CO$_2$H (200 ml) and then eluted with acetonitrile/CH$_3$CO$_2$H/water (8:1:1) (300 ml) in the column of "HP-20." The eluent was concentrated and freeze-dried with 1CH$_3$CO$_2$H. It was further purified as follows:

1. CM-cellulose columnn ($\phi$2.1 ×28 cm) purification: linear gradient elution of 0.06M-AcONH$_4$ (pH 4.8) →0.6M-AcONH$_4$ (pH 4.8) (each 400 ml). Yield: 100 mg:
2. "HP-20" column ($\phi$2.4 ×22 cm) purification: linear gradient elution of 0% CH$_3$CN/1% CH$_3$CO$_2$H →25% CH$_3$CN/1%CH$_3$CO$_2$H (each 400 ml). Yield: 60 mg.
3. "LH-20" column ($\phi$2.13 ×64 cm) purification:

It was eluted with 1N CH$_3$CO$_2$H to give the purified product (36 mg, 9.5%).

Amino acid analysis:

NH$_3$:1.28×2, Arg:1.03 ×4, Asp:1.00,Ser:0.91×4, Glu:1.00, Gly:1.00×5, Ala:1.01, ½(Cys)$_2$:0.82×2, Met-:o,81, Ile:0.90, Leu:0.97, Tyr:0.97, Phe:1.00 ×2

Example 13

Synthesis of α-hANP(7-27)

Boc-Arg(Tos)-Met-Asp-(OChx)-Arg(Tos)-Ile-Gly-Ala-Gln-Ser(Bzl)-Gly-Leu-Gly-Cys(4-CH$_3$Bzl)-Asn-Ser(Bzl)-Phe-Arg(Tos)-OBzl (724 mg, 0.25 mmole) was treated with TFA (10 ml) for 10 minutes while cooling and for 40 minutes at room temperature, and then 5.9N HCl/dioxane (0.2 ml, 5 times mmole) was added thereto. The solvent and excess acid were distilled off. Et$_2$O was added the residue and the thus-produced powder was obtained by filtration and dried overnight under reduced pressure over NaOH.

This powder, together with Boc-Cys(4CH$_3$Bzl)-Phe-Gly-Gly-OH (154 mg, 1.05 times mole) and HOBt (37 mg, 1.1 times mole), was dissolved in N-methylpyrolidone (NMP) (10 ml). WSCI (50 μl, 1.1 times mole) was added dropwise thereto while cooling, and the solution was stirred overnight. On the next day, the gelled solution produced a negative fluorescamine test.

Water was added to the solution and the solution was filtrated to obtain the solid material. It was washed with water, n-hexane, and Et$_2$O, in order, and dried. It was suspended in DMF and MeOH was added thereto. The solid material was obtained by filtration, and dried over P$_2$O$_5$ to give the protected and non-cyclized ANP(7-27), yielding 735 mg (87.4%).

Amino acid analysis:

Arg:0.97×3, Asp:0.99×2, Ser:0.87×2, Glu:1.02, Gly:0.99×2, Ala:1.02, Cys:0.34×2, Met:0.72, Ile:0.92, Leu:1.00, Phe:0.97×2

Elementary analysis: Found: C 57.03%, H 6.38%, N 13.08% Calculation: C 57.02%, H 6.39%, N 13.22% as C$_{161}$H$_{212}$O$_{36}$N$_{32}$S$_6$.1.5H$_2$O.

The peptide involving the protecting group as mentioned above (437 mg, 0.13 mmole) was treated with TFA (5 ml) for 60 minutes, and 5N HCl/dioxane (0.1 ml) was added thereto. The solvent was distilled off. To the residue, Et$_2$O was added, and the precipitated powder was obtained by filtration and dried overnight on NaOH. The powder was treated with HF (7 ml) in the presence of anisole (1.25 ml) while cooling to −2° to −1° C. for 60 minutes. The excess HF was distilled off. The residue was dissolved in 30% AcOH, washed three times with Et$_2$O , and passed through the column of the resin "Dowex 1×2" (AcO$^-$, 45 ml). It was eluted with 1AcOH, and the fractions that were positive in the Pauly test were collected, combined together, and freeze-dried. The thus-obtained 2SH derivative was converted to disulfide derivative by conventional cyclization method. It was purified by the following method:

1. CM-Celluose column chromatography: eluting agent 0.05M (pH 4.7) →0.45M (pH 4.8) NH$_4$OAC.
2. "HP-20" column chromatography: eluting agent 0→23% CH$_3$CN/5% AcOH.
3. Sephadex "LH-20" column chromatography: eluting agent 0.5N AcOH to obtain the object and purified product (29 mg).

Amino acid analysis:

Arg:1.04×3, Asp:1.00×2, Ser:0.90×2, Glu:0.97, Gly:1.00×5, Ala:1.00, Cys:0.87×2, Met:0.86, Ile:0.95, Leu:0.97, Phe:1.00×2

Elementary analysis: Found: C 46.37%, H 6.69%, N 18.00% Calculation: C 46.23%, H 6.74%, N 18.16% as C$_{91}$H$_{144}$O$_{28}$N$_{32}$S$_3$.2AcOH.8H$_2$O.

Example 14

Synthesis of [D-Ala$^9$]α-hANP (7-28)

(1) Synthesis of Boc-D-Ala-Gly-OBzl

Boc-D-Ala-OH (5.68 g, 30 mmole) and H-Gly-OBzl.TosOH (10.6 g, 1.05 eq) were suspended in CH$_2$Cl$_2$. WSCI (6 ml, 1.1 eq) was added dropwise while cooling, and the solution was stirred overnight. The CH$_2$Cl$_2$ was distilled off. The residue was dissolved in AcOEt (500 ml); washed with 1N HCl, water, 5% NaHCO$_3$, and water in order; and dried over Na$_2$SO$_4$. AcOEt was distilled off, and the residue was recrystalized twice with AcOEt/n-hexane to give the desired product (9.16 g, 90.7%).

(2) Synthesis of Boc-Phe-D-Ala-Gly-OBzl

Boc-D-Alal-Gly-OBzl (3.36 g, 10 mmole) was stirred with TFA (10 ml) for 10 minutes while cooling and for 30 minutes at room temperature, and then 5.0N HCl/dioxane (2.4 ml, 1.2 eq) was added. The solvent was distilled off, and Et$_2$O-n-hexane was added to the residue to give an oily substance. After decantation, the resulting substance was dried over NaOH for 3 hours. The obtained substance, together with Boc-Phe (2.65 g, 1 eq) and HOBt (1.42 g, 1.05 eq) was dissolved in DMF (12 ml). WSCI (1.92 ml, 1.05 eq), was added dropwise while cooling, and the solution was stirred overnight. To the solution, AcOEt (150 ml) was added. The solution was washed with 1HCl, water, 5% NaHCO$_3$ and H$_2$O in order, and was dried over Na$_2$SO$_4$. AcOEt was distilled off, and the residue was recrystalized with AcOEt/Et$_2$O and MeOH/Et$_2$O to give the desired product (2.57 g).

(3) Synthesis of Boc-Phe-D-Ala-Gly-OH

Boc-Phe-D-Ala-Gly-OBzl (2.4 g, 4.96 mmole) was dissolved in MeOH (50 ml), and H$_2$ gas was passed through the solution in the presence of Pd-C for 4 hours. Pd-C was removed by filtration, and MeOH was distilled off. To the thus-obtained residue MeOH/Et$_2$O and N-hexane were added. The thus-precipitated powder was separated by filtration and reprecipitated with AcOEt/n-hexane to obtain the desired product (1.95 g, 100%). (4) Synthesis of Z-Cys(4-CH$_3$Bzl)-Phe-D-Ala-Gly-OH Boc-Phe-D-Ala-Gly-OH (1.58 g, 4 mmole) was treated with TFA (10 ml) for 10 minutes while cooling and for 30 minutes at room temperature. The excess TFA was distilled off. To the residue, Et$_2$O was added. The thus-produced powder was obtained by filtration and dried for 6 hours over NaOH. It was suspended in the mixtured solvent of DMF (5 ml)-NMP (30 ml), and NEt$_3$ (0.56 ml) was added thereto while cooling. After that, Z-Cys(4-CH$_3$Bzl)-OSu (2 g, 1.1 eq) was added, and the mixture was stirred overnight. This transparent solution produced a negative fluorescamine test and was poured into diluted aqueous HCl. The thus-produced powder was obtained by filtration, washed with water and n-hexane, and dissolved in the mixed solvent of MeOH-CHCl$_3$. The solution was dehydrated by flashing with toluene and reprecipitated twice with AcOEt/Et$_2$O and n-hexane to give the powder of the object product (1.86 g, 72.4%).

Amino acid analysis:
Gly:0.99, Ala:1.00, Cys:small peak, Phe:1.00
Elementary analysis: Found: C 61.88%, H 6.04%, N 9.03% Calculation: C 62.00%, H 6.07%, N 8.76% as C$_{33}$H$_{38}$O$_7$N$_4$S.$\frac{1}{4}$H$_2$O.

(5) Synthesis of Protected [D-Ala$^9$]α-hANP(7-28)

Boc-Arg(Tos)-Met-Asp(Chex)-Arg(Tos)-Ile-Gly-Ala-Gln-Ser(Bzl)-Gly-Leu-Gly-Cys(4CH$_3$Bzl)-Asn-Ser(Bzl)-Phe-ARg(Tos)-Tyr(Cl$_2$Bzl)-OBzl (644 mg, 0.2 mmole) was stirred with TFA (5 ml) for 10 minutes while cooling and for 50 minutes at room temperature, and then 5.0N HCl/dioxane (0.1 ml) was added thereto. The solvent was distilled off, and to the residue, Et$_2$O was added to make a powder. The powder was obtained by filtration and dried overnight over NaOH. The powder, together with Z-Cys(4CH$_3$Bzl)-Phe-D-Ala-Gly-OH (133 mg, 1.05 eq) and HOBt (30 mg, 1.1 eq), was dissolved in NMP (8 ml). WSCI (41 μl, 1.1 eq) was added while cooling, and the solution was stirred for 6 hours. Water was added to the gelled solution, which produced a negative fluorescamine test. The thus-obtained solution was filtrated, and the obtained solid material was washed with water, n-hexane, Et$_2$O, and MeOH, in order, and dried. The material was suspended in DMF, and MeOH was added thereto. The solution was filtrated. The obtained solid material was washed with MeOH to obtain the object product (640 mg, 85.7%).

Amino acid analysis:
Arg:1.01×3, Asp:1.00×2, Ser:0.89×2, Glu:1.01, Gly:1.00×4, Ala:1.00×2, Cys:small peak, Met:0.64, Ile:0.96, Leu:0.99, Tyr:0.86, Phe:0.98×2
Elementary analysis: Found: C 57.62%, H 6.10%, N 12.03% Calculation: C 57.66%, H 6.12%, N 12.26% as C$_{181}$H$_{225}$O$_{38}$N$_{86}$S$_6$Cl$_2$.2H$_2$O (6) Synthesis of [D-Ala$^9$]α-hANP(7-28)

The protected peptide (485 mg, 0.13 mmole) was treated with HF (7 ml) in the presence of anisole (1.25 ml) at −1° C. for 60 minutes. The excess HF was distilled off. The thus-obtained residue was dissolved in 2N AcOH, and the solution was washed 3 times with Et$_2$O, passed through the column of the resin "Dowex 1×2" (AcO$^-$, 50 ml), and eluted with 1AcOH. The obtained eluent was freeze-dried. The thus-obtained 2SH derivative was cyclized by conventional method to give the disulfide derivative in the crude form. This derivative was purified by the following method:

1. CM-cellulose column chromatography: 0.05M (pH 4.7)→0.5M (pH 4.8), NH$_4$AC.
2. "HP-20" column chromatography: 0→28% CH$_3$CN/5% AcOH.
3. Sephadex "LH-20" column chromatography: 0.5N AcOH to obtain the object and purified product (23 mg).

Amino acid analysis:
Arg:1.00×3, Asp:1.02×2, Ser:0.92×2, Glu:1.00, Gly:1.03×4, Ala:1.00×2, Cys:0.82×2, Met:0.83, Ile:0.95, Leu:0.99, Tyr:0.95, Phe:1.02×2
Elementary analysis: Found: C 46.41%, H 6.75%, N 16.73% Calculation: C 46.26%, H 6.84%, N 16.96% as C$_{101}$H$_{155}$O$_{30}$N$_{33}$S$_3$.2AcOH.11H$_2$O Example 15

Synthesis of [Des Gly$^9$]α-hANP(7-28)

(1) Synthesis of Boc-Phe-Gly-OBzl

Boc-Phe-OH (79.6 g, 0.3 mole), Gly-OBzl-TosOH (111 g, 1.1 eq), and HOBt (44.6 g, 1.1 eq) were dissolved in DMF (300 ml). WSCI (60.4 ml, 1.1 eq ) was added dropwise while cooling, and the solution was stirred overnight. DMF was distilled off. The residue was dissolved in CHCl$_3$, and the solution was washed with 5% NaHCO$_3$, 10% Na$_2$CO$_3$, water, 1HCl, and water, in order, and dried over MgSO$_4$. The CHCl$_3$ was distilled off, and to the residue, Et$_2$O was added. The thus-produced powder was obtained by filtration and recrystalized two times with AcOEt/Et$_2$O to obtain the object product (59 g).

(2) Synthesis of Boc-Phe-Gly-OH

Boc-Phe-Gly-OBzl (6.2 g, 15 mmole) was suspended in the mixtured solvent of MeOH (80 ml) and AcOH (30 ml), and then H$_2$ gas was passed through the solution in the presence of Pd-C for 4 hours. Pd-C was removed by filtration, and the solvent was distilled off. The thus-obtained residue was recrystalized two times with AcOEt/n-hexane to obtain the object product (4.49 g, 92.8%).

(3) Synthesis of Z-Cys(4-CH$_3$Bzl)-Phe-Gly-OH

Boc-Phe-Gly-OH (1.29 g, 4 mmole) was stirred with TFA (10 ml) for 10 minutes while cooling and for 25 minutes at room temperature, and TFA was distilled off. The residue was treated with Et$_2$O-n-hexane. The thus-produced powder was obtained by filtration, dried for 2.5 hours over NaOH, dissolved in DMF (9 ml), and then neutralized with NEt$_3$ while cooling. Z-Cys(4CH$_3$Bzl)-OSu (2.1 g, 1.15 eq) was added thereto, and the solution was stirred for 20 hours. AcOEt (50 ml) was added thereto and the solution was washed with 1HCl and with water and then dried over Na$_2$SO$_4$. AcOEt was distilled off and the residue was treated twice with AcOEt, MeOH, Et$_2$O , and n-hexane to give powder of the object product (1.5 g, 66.7%).

Amino acid analysis:
Gly:1.00, Cys:small peak, Phe:0.99
Elementary analysis: Found: C 63.89%, H 6.05%, N 7.46% Calculation: C 63.92%, H 5.90%, N 7.45% as C$_{30}$H$_{33}$O$_6$N$_3$S.

(4) Synthesis of Protected [DesGly⁹]α-hANP-(7-28)

Boc-Arg(Tos)-Met-Asp(CHex)-Arg(Tos)-Ile-Gly-Ala-Gln-Ser(Bzl)-Gly-Leu-Gly-Cys(4-CH₃Bzl)-Asn-Ser(Bzl)-Phe-Arg(Tos)-Tyr(Cl₂Bzl)-OBzl (644 mg, 0.2 mmole) was treated with TFA (5 ml) for 10 minutes while cooling and for 40 minutes at room temperature, and then 5.0N HCl/dioxane (0.1 ml) was added. The solvent was distilled off. Et₂O was added. The thus-produced powder was obtained by filtration and dried overnight on NaOH.

This powder together with Z-Cys(4-CH₃Bzl)-Phe-Gly-OH (118 mg, 1.05 eq) and HOBt (30 mg, 1.1 eq, was dissolved in NMP (8 ml). WSCI (41 μl, 1.1 eq) was added while cooling, and the solution was stirred overnight. Water was added to the gelled solution, which produced a negative fluorescamine test. The solution was filtrated. The thus-obtained solid material was washed with water and with Et₂O and suspended in DMF, MeOH was then added. The solution was filtrated, and the thus-obtained solid material was washed with MeOH to give the object product (640 mg, 87.3%).

Amino acid analysis: Arg:1.00×3, Asp:1.00×2, Ser:0.90×2, Glu:1.05, Gly:1.00×4, Ala:1.00, Cys:small peak, Met:0.58, Ile:0.97, Leu:1.01, Tyr:0.80, Phe:0.95×2

Elementary analysis: Found: C 57.72%, H 6.46%, N 11.64% Calculation: "C 57.51%, H 6.13%, N 12.06% as C₁₇₈H₂₂₀O₃₇N₃₂S₆Cl₂·3H₂O.

(5) Synthesis of [DesGly9]α-hANP(7-28)

The object and purified product (30.7 mg) was obtained in the same manner as in Example 14 (6) using as a starting material the protected peptide produced above (5) (476 mg, 10.13 mmole).

Amino acid analysis:
Arg:1.01×3, Asp:1.00×2, Ser:0.90×2, Glu:0.97, Gly:1.01×4, Ala:1.01, Cys:0.86×2, Met:0.81, Ile:0.94, Leu:0.99, Tyr:0.95, Phe:1.01×2

Elementary analysis: Found: C 46.21%, H 6.58%, N 16.86% Calculation: C 46.46%, H 6.80%, N 17.00% as C₉₈H₁₅₀O₂₉N₃₂S₃·2AcOH·10H₂.

Example 16

Synthesis of [D-Asp¹³]α-hANP(7-28)

(1) Synthesis of
Boc-D-Asp(OBzl)-Arg(Tos)-Ile-Gly-OPac

Boc-Arg(Tos)-Ile-Gly-OPac (1 g, 1.39 mmole) was stirred with TFA (10 ml) for 50 minutes. TFA was distilled off. To the residue, 5.9N HCl/dioxane (0.35 ml, 2.1 mmole) was added, and stirred well. Et₂O was then added. The thus-produced precipitate was obtained by filtration, dried, and dissolved in DMF (8 ml). HOBt (216 mg, 1.6 mmole), Boc-D-Asp(OBzl)-OH (517 mg, 1.6 mmole), and WSCI (0.29 ml, 1.6 mmole) were added to the solution while cooling to −15° C. The solution was stirred for 3 hours to complete the reaction, and water was added. The thus-produced precipitate was obtained by filtration and reprecipitated with MeOH-Et₂O to obtain the object product (1.1 g, 86.6%).

(2) Synthesis of
Boc-Met-D-Asp(OBzl)-Arg(Tos)-Ile-Gly-OPac

A mixture of Boc-D-Asp(OBzl)-Arg(Tos)-Ile-Gly-OPac (1 g, 1.08 mmole) and TFA (10 ml) was stirred for 50 minutes. TFA was distilled off, and to the residue, 5.9N HCl/dioxane (0.28 ml, 1.62 mmole) was added and stirred well. Et₂O was then added. The thus-produced precipitate was obtained by filtration, dried, and then dissolved in DMF (10 ml). HOBt (162 mg, 1.2 mmole), Boc-Met-OH (299 mg, 1.2 mmole), and WSCI (0.22 ml, 1.2 mmole) were added thereto while cooling to −15° C. The solution was stirred for 5 hours, and water was added. The thus-produced precipitate was obtained by filtration and reprecipitated with MeOH-Et₂O to obtain the object product (960 mg, 84.2%).

(3) Synthesis of
Boc-Arg(Tos)-Met-D-Asp(OBzl)Arg(Tos)-Ile-Gly-OPac

The object product (750 mg, 64.7%) was obtained in the same manner as above (2), using as starting materials Boc-Met-D-Asp(OBzl)-Arg(Tos)-Ile-Gly-OPac (0.9 g, 0.85 mmole) and Boc-Arg(Tos)-OH (471 mg, 1.1 mmole).

(4) Synthesis of
Boc-Cys(4-CH₃Bzl)-Phe-Gly-Gly-Arg(Tos)-Met-D-Asp(OBzl)-Arg(Tos)-Ile-Gly-OPac A mixture of Boc-Arg(Tos)-Met-D-Asp(OBzl)Arg-(Tos)-Ile-Gly-OPac (650 mg, 0.48 mmole) and TFA (5 ml) was stirred for 50 minutes. TFA was distilled off, and to the residue, 5N HCl/dioxane (0.14 ml, 0.72 mmole) was added and stirred well. Et₂O was added thereto. The thus-produced precipitate was obtained by filtration, dried, and dissolved in DMF (5 ml). HOBt (72 mg, 0.53 mmole), Boc-Cys(4-CH₃Bzl)-Phe-Gly-Gly-OH (311 mg, 0.53 mmole), and WSCI (0.1 ml, 0.53 mmole) were added thereto while cooling to −15° C. and then stirred for 4 hours. To the reaction solution, water was added. The thus-produced precipitate was obtained by filtration and reprecipitated with MeOH to obtain the object product (720 mg, 81.9%).

(5) Synthesis of
Boc-Cys(4-CH₃Bzl)-Phe-Gly-Gly-Arg(Tos)-Met-D-Asp(OBzl)-Arg(Tos)-Ile-Gly-OH The peptide produced above (4) (690 mg, 0.37 mmole) was dissolved in AcOH (40 ml), and the solution was stirred for 1 hour in the presence of zinc-powder (1 g) at 45° C. Zinc-powder was removed by filtration, and AcOH was distilled off. To the residue, water was added, and the thus-produced precipitate was obtained by filtration and recrystalized with MeOH to obtain the object product (500 mg, 78.9% ).

(6) Synthesis of Protected [D-Asp¹³]-α-hANP(7-28)

Boc-Cys(4-CH₃Bzl)-Phe-Gly-Gly-Arg(Tos)-Met-D-Asp(OBzl)-Arg(Tos)-Ile
-Gly-Ala-Gln-Ser(Bzl)-Gly-Leu-Gly-Cys(4-CH₃Bzl)-Asn-Ser(Bzl)-Phe-Arg(Tos)Tyr(Cl₂Bzl)-OBzl

A mixture of Boc-Ala-Gln-Ser(Bzl)-Gly-Leu-Gly-Cys(4-CH₃Bzl)-Asn-Ser(Bzl)-Phe-Arg(Tos)-Tyr(Cl₂Bzl)-OBzl (170 mg, 0.081 mmole) and TFA (5 ml) was stirred for 50 minutes. TFA was distilled off. To the residue, 5.0N HCl/dioxane (3.0 μl, 0.13 mmole) was added and stirred well. Et₂O was added thereto. The thus-produced precipitate was obtained by filtration and dissolved in NMP (8 ml). HOBt (13.5 mg, 0.1 mmole) and the peptide as obtained above (5) (160 mg, 0.1 mmole) were added while cooling to −15° C. The solution was stirred for 16 hours, and then water was added to the reaction solution. The thus-produced precipitate was obtained by filtration and refluxed twice with MeOH to obtain the object product (280 mg, 94.5%).

(7) Synthesis of [D-Asp$^{13}$]-α-hANP(7-28)

A mixture of the protected [D-Asp$^{13}$]-α-hANP(7-28) (270 mg, 0.073 mmole) and TFA (5 ml) was stirred for 50 minutes. TFA was distilled off, and to the residue, Et$_2$O was added. The thus-produced precipitate was obtained by filtration and dried on NaOH in the desiccator for 16 hours. To the precipitate, anisole (0.5 ml) and HF (5 ml) were added. The material was stirred for reaction for 60 minutes at −1° C. HF was distilled off, and to the residue, Et$_2$O , was added. The thus-produced precipitate was obtained by extraction with 2N AcOH. It was washed with Et$_2$O and passed through the column of the resin "Dowex 1×2" (AcO$^-$), and the obtained eluent was freeze-dried. All of the thus-obtained powder was dissolved in 1AcOH (8 ml), and the solution was added dropwise to the mixtured solution of 1M NH$_4$OAc/8M urea (72 ml) and K$_3$Fe(CN)$_6$ (34 mg, 0.102 mmole) over 20 minutes. In this case, the pH value of the reaction solution was kept to 7.4 with 10% NH$_4$OH. The reaction solution was later adjusted to pH 4.5 with AcOH passed through the column of the resin "IRA-45" (Cl$^-$, 50 ml), and was with 1AcOH. The washings were desalted in the column of the resin "Diaion HP-20", and the obtained eluent was freeze-dried. All of the obtained powder was purified by CM-cellulose column chromatography in the gradient elution with 0.05M NH$_4$OAc (pH 5) (500 ml)→0.4M NH$_4$OAc (pH 6) (500 ml). Fractions 35 to 42 were collected, combined together, and freeze-dried. The material was further purified by "Diaion HP-20" column chromatography (elution with 5% →25%CH$_3$CN/5% AcOH). Fractions 75 to 87 were collected, combined together, and freeze-dried. The thus-obtained powder was dissolved in 1AcOH and passed through the column of the resin "Dowex 1×2" (AcO$^-$), and the obtained eluent was freeze-dried.

The thus-obtained powder was desalted by the column of the resin "LH-20" and eluted with 1AcOH. The obtained eluent was freeze-dried to give the object product (21 mg).

Amino acid analysis:
NH$_3$:2.66, Arg:1.03×3, Asp:1.00×2, Ser:0.89×2, Glu:0.96, Gly:1.01×5, Ala:1.00, ½(Cys)$_2$:0.83×2, Met:0.85, Ile:0.95, Leu:0.97, Tyr:0.95, Phe:1.00×2

High-performance liquid chromatography (HPLC):
Column: Nucleosil 5 C$_{18}$;
Eluting solvent: 25% CH$_3$CN/O. 1% TFA
Time: 62 minutes Example 17

Pharmaceutical Activity

For peptides produced in the above-mentioned examples, diuretic tests were carried out.

Example 17 Tests of Pharmacological Activity

| Compound | Sample (Example No.) | Spasmolytic Activity$^a$ in Rat Aorta | Spasmolytic Activity$^a$ in Chick Rectum | Natriuretic Activity in Anesthetized Rat |
|---|---|---|---|---|
| α-hANP[1-28] | (Control) | 100 | 100 | ++ |
| α-hANP[5-28] | (Ex. 2) | 110 ± 7.6 (5) | 73.6 ± 1.9 (2) | + |
| α-hANP[7-28] | (Ex. 5) | 148 ± 24.5 (6) | 443 ± 7.5 (2) | +++ |
| α-hANP[5-27] | (Ex. 1) | 103 ± 25.5 (4) | 60.3 ± 5.1 (2) | +++ |
| α-hANP[5-25] | (Ex. 4) | 6.67 ± 1.23 (4) | 30.7 ± −3.6 (6) | + |
| [Nle$^{12}$]-α-hANP[1-28] | (Ex. 3) | 80.5 ± 12.2 (4) | 70.3 ± 10.9 (2) | |
| Met(O)$^{12}$-α-hANP[1-28] | (Ex. 7) | 4.72 ± 0.70 (4) | 2.89 ± 0.67 (4) | |
| Asu$^{7,23}$-α-hANP[7-23] | (Ex. 6) | 1.03 ± 0.48 (3) | 105 ± 18 (4) | + |
| [Met$^{12}$,Asu$^{7,23}$]-α-hANP[7-28] | (Ex. 8) | 10.9 ± 0.65 (6) | 82 ± 8.3 (4) | + |
| [Ile$^{12}$,Asu$^{7,23}$]-α-hANP[7-28] | (Ex. 9) | 124 ± 4.2 (2) | 90.9 ± 3.0 (6) | +++ |
| [Nle$^{12}$,Asu$^{7,23}$]-α-hANP[7-28] | (Ex. 10) | 7.5 ± 0.9 (2) | 37.6 ± 4.5 (2) | + |
| [Nle$^{12}$]-α-hANP[7-28] | (Ex. 11) | 57 ± 3 (4) | 189 ± 10 (2) | +++ |
| α-hANP[4-28] | (Ex. 12) | 61 ± 3 (2) | 56 ± 4 (2) | ++ |
| α-hANP[7-27] | (Ex. 13) | 73.7 (2) | 200 (5) | ++ |
| [D-Ala$^9$]-α-hANP[7-28] | (Ex. 14) | 121 (4) | 344 (3) | +++ |
| [DGly$^9$]-α-hANP[7-28] | (Ex. 15) | 0.2 (2) | 2.3 (3) | − |
| [D-Asp$^{13}$]-α-hANP[7-28] | (Ex. 16) | 0.4 (2) | 1.9 (3) | − |

Values are: Mean ± standard error; Number of experiment are in parentheses.
$^a$50% effective dose (ED50) for each preparation was obtained, and the ratio was calculated to the standard hANP (1-28)

Test Methods:
Assay of the pharmacological activity of ANP.
(1) Spasmolytic activity in rat aortic strips.

Male Sprague-Dawley rats weighing 250–280 g were used. After the rats were decapitated, their thoracic aorta were obtained and aortic helical strips were prepared. Krebs solution was used in this assay system. The aortic strips were suspended in a 20 ml organ-bath which was aerated with 5% carbon dioxide and 95% oxygen and kept at 37° ±0.5° C. The aortic tension was recorded isotonically. The isotonic recording system, consisted of a transducer and amplifier (ME commercial ME4012) and a recorder (Sanei 8K21). A resting tension of 0.5 g was loaded on the aortic strips. The prepared strips were left under the described conditions for 1 hour to obtain the stable tension. The aortic preparation contracted with norepinephrine (5×10$^{-8}$M) was exposed to ANP to examine its relaxant activity. The dose response curve was obtained for the α-hANP(1-28) and the ANP fragment in the same preparation. The 50% effective dose (ED50) for each preparation was obtained and the ratio was used as the specific activity.
(2) Spasmolytic activity in chick rectum.

Male, 2- to 3-week-old chicks weighing 155–175 g were used. After the chicks were anesthetized with pentobarbital (6 mg/kg, ip), their rectums were excised. Krebs solution was used. The rectums were suspended in 20 ml organ-bath aerated with 5% carbon dioxide and 95% oxygen and kept at 37° ±0.5° C. Contractile tension of the rectum was determined isotonically. The isotonic recording system used was the same as that used in testing the rat aortic preparations. The rectal preparations were stabilized by keeping them under 0.5 g of tension conditions for 1 hour. The rectal preparations contracted with carbachol ($2 \times 10^{-7}$M), were exposed to ANP to examine its relaxing effect. As with the rat aortic preparations, ED50 for the standard α-haNP(1-28) and for the ANP fragment were determined, and the specific activity were calculated.

(3) Natriuretic activity in anesthetized rats.

Male Sprague-Dawley rats weighing 250–300 g were used. After the rats were anesthetized by intraperitoneal administration of 50 mg/kg pentobarbital, a cannula was inserted into the trachea to maintain the airway. The blood pressure and heart rate were recorded through a cannula inserted into the femoral artery. The recording system, consisted of a blood pressure transducer (Century Technology, CP-01), an amplifier (Star Medical, PA-011), a heart rate counter (Star Medical, HR-001), and a recorder (Rika Denki, R-302).

Ringer's solution was infused through a cannula inserted into the femoral vein at the rate of 20 μl/min using a perfusion pump (Ikouseiki, M-IV). ANP was administered through this cannula.

A cannula was inserted into the bladder, urine samples were collected into the 2ml sampling tube at 10-minute intervals. The urine volume was measured by weighing it with an automatic balance (Metler, AE160). Sodium and potassium concentrations were determined using the 20 μl of urine obtained, by a glass electrode ion concentration meter (Orion research 901).

What is claimed as new and desired to be secured by Letters Patent of the United States is:

1. A peptide having the formula

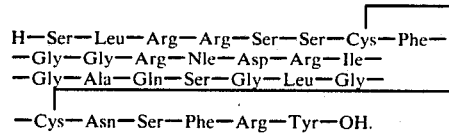

2. A peptide having the formula

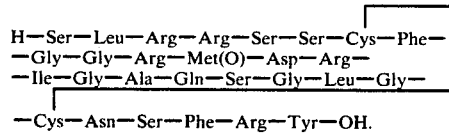

3. A peptide having the formula

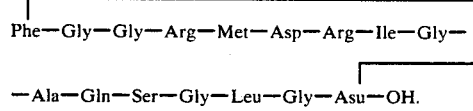

* * * * *

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

Column 5, line 3, change "glutamine,Ser" to --glutamine, Ser--;

line 29, change "pyrolidone," to --pyrrolidone--.

Column 6, line 14, change "9 mmole" to --9 mmole)--;

line 17, change "therto" to --thereto--;

line 25, change "overnight" to --overnight;--;

line 66, change "OEt.HCl" to --OEt·HCl--.

Column 7, line 7, change "1 N HaOH" to --1N NaOH--.

Column 9, line 45, change "were" to --was--;

line 47, change "fluorolescamine" to --fluorescamine--;

line 54, change "recrystalized" to --recrystallized--.

Column 10, line 1, change "crystalized" to --crystallized--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

It is certified that error appears in the above-identified patent and that said Letters Patent is hereby corrected as shown below:

line 14, change "recrystalized" to --recrystallized--;

line 17, change "product (5.4 g)" to --product. (5.4 g)--;

line 28, change "crystalized" to --crystallized--;

line 38, change "fluorolescamine" to --fluorescamine--;

line 47, change "recrystalized" to --recrystallized--;

line 60, before "dropwise" insert --added--;

line 64, change "(0.30 g, 0.05 eg)," to --(0.30 g, 0.05 eq),--;

line 66, change "fluoroscamine" to --fluorescamine--.

UNITED STATES PATENT AND TRADEMARK OFFICE
CERTIFICATE OF CORRECTION

PATENT NO. : 4,670,540

DATED : June 2, 1987

INVENTOR(S) : Sakakibara

It is certified that error appears in the above-identified patent and that said Letters Patent is hereby corrected as shown below:

Column 11, line 20, change "fluorolescamine" to --fluorescamine--;

line 40, change "fluoroscamine" to --fluorescamine--.

Column 12, line 5, change "Boc-Arg(Tos)MetAsp(Bzl)Arg(Tos-" to --Boc-Arg(Tos)MetAsp(Bzl)Arg(Tos)- --;

line 6, change ")IleGly-OH" to --IleGly-OH--;

line 12, change "fluoroscamine" to --fluorescamine--;

line 34, change "recrystalized" to --recrystallized--;

line 50, change "recrystalized" to --recrystallized--;

line 57, change "3.5 N NCl/dioxane" to --3.5N HCl/dioxane--;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 66, change "recrystalized" to --recrystallized--.

Column 13, line 18, change "g, 20 mmole). WSCI" to --g, 20 mmole), and WSCI--;

line 22, change "recrystalized" to --recrystallized--;

line 35, change "(3.7 g, 12.5 mmole). WSCI" to --(3.7 g, 12.5 mmole), and WSCI--;

line 39, change "recrystalized" to --recrystallized--;

line 43, change "(4-MeBZL)" to --(4-MeBzl)--;

line 44, change "(4-MeBZL)" to --(4-MeBzl)--;

line 59, change "(4MeBzyl)" to --(4-MeBzl)--.

Column 14, line 39, change "AcO$^-$, Volume:" to --AcO$^-$ (Volume:--.

Column 15, line 9, change "(AcO_," to --(AcO$^-$,--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

Page 5 of 24

It is certified that error appears in the above-identified patent and that said Letters Patent is hereby corrected as shown below:

line 28, change "(Tos)Tyr($C_2$Bzl)-OBzl" to --(Tos)Tyr($Cl_2$Bzl)-OBzl--;

line 29, delete "H-Tyr(C";

line 30, change "Tyr $Cl_2$Bzl)-OBzl. HCl" to --H-Tyr($Cl_2$Bzl)-OBzl·HCl--;

line 32, change "$CH_2Cl_{12}$" to --$CH_2Cl_2$--;

line 64, change "NaHCO," to --$NaHCO_3$,--.

Column 16, line 22, change "crystalize." to --crystallize.--;

line 23, change "talized" to --tallized--;

line 43, change the boldface "1.15" to regular typestyle --1.15--;

line 55, change "3.5 N Cl" to --3.5N HCl--.

Column 17, line 14, change "(4-Me-Bzl)" to --(4-MeBzl)--;

line 16, change "them" to --then--;

line 17, change "3.5 NHCl" to --3.5N HCl--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

Page 6 of 24

It is certified that error appears in the above-identified patent and that said Letters Patent is hereby corrected as shown below:

line 24, change "(70 ml) WSCI" to --(70 ml). WSCI--;

line 25, change "(PH" to --(pH--;

line 27, change "homogenous" to --homogeneous--.

Column 18, line 8, change the boldface "0.96" to regular typestyle --0.96--;

line 13, change "$C_{153}H_{197}O_{34}N_{29}S_5Cl_2 \cdot 2.5H_2O$" to --$C_{153}H_{197}O_{34}N_{29}S_5Cl_2 \cdot 2.5H_2O$--;

line 16, change "(Tos)MetAsp(OBzl)Arg(Tos)" to --(Tos)MetAsp(OBzl)Arg(Tos)- --;

line 67, change " "HP- —20 " to --"HP-20"--.

Column 19, line 16, change "(Tos)}NleAsp" to --(Tos)NleAsp--;

line 50, change "(40 mg)." to --(40 mg), and--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

It is certified that error appears in the above-identified patent and that said Letters Patent is hereby corrected as shown below:

line 58, change "(30)" to --(39--.

Column 20, line 8, change "Nle: 1.0" to --Nle: 1.01--;

line 22, change "mmole). WSCI" to --mmole), and WSCI--;

line 26, change "recrystalized" to --recrystallized--;

line 40, change "2.5 mmole). WSCI" to --2.5 mmole), and WSCI--;

line 50, change "(Bzl-" to --(Bzl)- --;

line 51, change ")Ser" to --Ser--;

line 57, change "15 ml" to --(15 ml)--;

line 67, change "recrystalized" to --recrystallized--.

Column 21, line 2, change "(Bzl-" to --(Bzl)- --;

line 3, change ")Cys" to --Cys--;

line 22, change "(Bzl-" to --(Bzl)- --;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 23, change ")Cys" to --Cys--;

line 24, change "(Bzl-" to --(Bzl)- --;

line 25, change ")Cys" to --Cys--;

line 54, change "DMP" to --DMF--.

Column 22, line 11, change "(4MeBz-" to --(4-MeBzl)- --;

line 12, change "1)Asn" to --Asn--;

line 24, change the boldface "0.47" to regular typestyle --0.47--;

line 41, change "$C_{240}H_{307}O_{51}N_{45}S_7Cl_2.2H_2O$" to --$C_{240}H_{307}O_{51}N_{45}S_7Cl_2 \cdot 2H_2O$--;

line 46, change the boldface "to" to regular typestyle --to--;

line 52, change "freezedried" to --freeze-dried--;

line 55, after "(cellulose)" insert --using as--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

It is certified that error appears in the above-identified patent and that said Letters Patent is hereby corrected as shown below:

line 56, change "(pH5.0" to --(pH 5.0--;

line 60, delete ".27% CH3CN/5% AcOH, and then by";

line 61, after "then" insert --by--.

Column 23, line 3, change "$C_{122}H_{194}O_{38}N_{44}S_2 \cdot 4H_2O$" to --$C_{122}H_{194}O_{38}N_{44}S_2 \cdot 4AcOH \cdot 14H_2O$--;

line 6, change "(5-25}" to --(5-25)--;

line 16, change "extractd" to --extracted--;

line 31, change "Agn" to --Asn--;

line 42, change "$MgSO_4$ The" to --$MgSO_4$. The--;

line 55, change "crystaline" to --crystalline--;

line 56, change "4MeBzl)" to --4-MeBzl)--;

line 66, delete "and" (first occurrence).

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

Column 24, line 40, change "15 ml NMF" to --(15 ml) and NMP--;

line 56, change "(4" to --(4-MeBzl)AsnSer(Bzl)-OBzl--;

line 61, change the boldface "g," to --g,-- (regular typestyle).

Column 25, line 31, change "were" to --was--;

line 41, change "Cl$^{31}$" to --Cl$^-$--;

line 44, change "Cl$^{31}$" to --Cl$^-$--;

line 51, change "substance," to --substance--.

Column 26, line 19, before "12H$_2$O" insert --AcOH·--;

line 24, change "Phe:096" to --Phe:0.96--;

line 31, change "actic" to --acetic--;

line 43, change "Arg (2Bzl)-OBzl" to --Arg-(Tos)Tyr(Cl$_2$Bzl)-OBzl--;

line 50, change "mmole" to --mmole)--;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 55, change "mmole). WSCI" to --mmole), and WSCI--, still line 55, after "mmole" (second occurrence) insert --)--;

line 56, change "added, to" to --added to--.

Column 27, line 4, change "(Cl2Bzl)" to --(Cl$_2$Bzl)--;

line 21, change "PH" to --pH--;

line 23, change "(Cl-20 ml)" to --(Cl$^-$, 20 ml)--;

line 25, change "(Cl-100 ml)" to --(Cl$^-$, 100 ml)--;

line 31, change "NH$_4$O Ac" to --NH$_4$OAc--;

line 40, change "6N Hcl" to --6N HCl--;

line 48, change "Asu$^{7,23}$)" to --(Asu$^{7,23}$)--;

line 54, change "HoBt" to --HOBt--, still line 54, change "was" to --were--.

Column 28, line 10, change "(10 ml" to --(10 ml)--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

Page 12 of 24

It is certified that error appears in the above-identified patent and that said Letters Patent is hereby corrected as shown below:

line 11, before "stirred" insert --was--;

line 37, change "(80-20-0.1" to --(80-20-0.1)--;

line 51, change "recrystalized" to --recrystallized--;

line 55, change "Boc-PheGlyGlyaAg" to --Boc-PheGlyGlyArg--;

line 56, after "Asu" insert -- - --.

Column 29, line 1, change "HoBt" to --HOBt--;

line 7, change "19" to --(19--;

line 15, change "2.3.g" to --2.3 g--;

line 46, change "Hcl" to --HCl--.

Column 30, line 14, change "WSCI.HCl" to --WSCI:HCl--;

line 17, change "WSCI. HCl" to --WSCI:HCl--;

line 24, before "the" insert --give--;

line 25, after "(68%)" insert --.--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

Page 13 of 24

It is certified that error appears in the above-identified patent and that said Letters Patent is hereby corrected as shown below:

line 35, change "Met(0)" to --Met(O)--;

line 56, change "reducecd" to --reduced--;

line 64, change "pH" to --(pH--;

line 65, change "Abuffer" to --A-buffer--.

Column 31, line 25, change "dissovled" to --dissolved--;

line 27, change "chromatogoraphy" to --chromatography--;

line 28, change "solvent'" to --solvent:--;

line 35, after "Ile:0.97" insert --,--;

line 45, change "(Nle12)" to --($Nle^{12}$)--;

line 48, change "(Cl2Bzl)" to --($Cl_2Bzl$)--;

line 55, change "N-methylpyrolidone" to --N-methylpyrrolidone--;

line 56, change "HoBt" to --HOBt--;

line 58, change "FµH1," to --µ1,--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

Page 14 of 24

It is certified that error appears in the above-identified patent and that said Letters Patent is hereby corrected as shown below:

line 59, change "hours, stirring" to --hours stirring,--.

Column 32, line 8, change the boldface "(7-28)" to --(7-28)-- (regular typestyle);

line 12, change "waFvHhed" to --washed--;

line 20, change "(CN)6" to --$(CN)_6$--;

line 28, change "was" to --were--;

line 31, change "thusobtained" to --thus-obtained--;

line 35, change "OAC" to --OAc--;

line 40, before "main" insert --The--;

line 41, change "freezedried" to --freeze-dried--;

line 51, change "(0)12" to --$(O)^{12}$--;

line 66, change "N-methyl pyrolidone" to --N-methylpyrrolidone--.

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

Column 33, line 4, change "solution," to --solution.--;

line 11, change "0 19" to --0.19--;

line 13, change "Met(O)12-o" to --Met(O)$^{12}$-α--;

line 19, change "(Cl2Bzl)" to --(Cl$_2$Bzl)--;

line 25, change "thusobtained" to --thus-obtained--;

line 34, change "K3Fe(CN)6" to --K$_3$Fe(CN)$_6$--;

line 58, change "OAcOH" to --O-AcOH--;

line 60, change "(O)12" to --(O)$^{12}$--, still
line 60, delete ",(1-28);";

line 62, change "1% 60%" to --1% —> 60%--;

line 68, change "Try" to --Tyr--.

Line 3, Column 34, change "[Met12, Asu7,23]" to --[Met$^{12}$, Asu$^{7,23}$]--;

line 4, change "1" to --(1)--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

Page 16 of 24

It is certified that error appears in the above-identified patent and that said Letters Patent is hereby corrected as shown below:

line 18, change "Nmethyl-" to --N-methyl- --;

line 19, change "pyrolidone" to --pyrrolidone--;

line 26, change "chloroformmethanol" to --chloroform/methanol--;

line 30, change "$NH_3 1.16$" to --$NH_3:1.16$--;

line 46, change "chloroformme-" to --chloroform/me- --;

line 64, change "mixtured" to --mixed--, still line 64, change "Nmethyl-" to --N-methyl- --;

line 65, change "pyrolidone" to --pyrrolidone--.

Column 35, line 8, change "GlyAsu" to --Gly-Asu--;

line 10, change "(Cl2Bzl)" to --($Cl_2Bzl$)--;

line 12, change "nole)" to --mmole)--;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 22, change "N-methylpyrolidone" to --N-methylpyrrolidone--;

line 42, change "($Cl_2$(Bzl)" to --($Cl_2$Bzl)--;

line 43, change "FvH mole" to --mmole--, still line 43, change "$CH_3CO$-" to --$CH_3CO_2H$--;

line 44, delete "FvHl";

line 67, change "20 µ," to --20 µl,--.

Column 36, line 4, change "1.1 mole)" to --1.1 times mole)--;

line 17, change "$Met^{12}$," to --[$Met^{12}$,--;

line 19, change "[Met12, Asu7,23]" to --[$Met^{12}$, $Asu^{7,23}$]--;

line 25, change "Aco$^-$," to --AcO$^-$,--;

line 31, change "AcONH4" to --$AcONH_4$--;

line 34, change "CHFvHCN/1NAcOH" to --$CH_3CN$/1N AcOH--;

Page 17 of 24

UNITED STATES PATENT AND TRADEMARK OFFICE
CERTIFICATE OF CORRECTION

PATENT NO. : 4,670,540

DATED : June 2, 1987

INVENTOR(S) : Sakakibara

Page 18 of 24

It is certified that error appears in the above-identified patent and that said Letters Patent is hereby corrected as shown below:

line 35, change "Yield'" to --Yield:--.

Column 37, line 11, change "gl," to --g,--;

line 30, after "(4)" insert --using--;

line 47, change "hANP7-28)" to --hANP(7-28)--;

line 54, change "$NH_3 1.23$" to --$NH_3$:1.23--;

line 55, delete "NH3:1.";

line 59, change "[Nle12, Asu7,23]" to --[$Nle^{12}$, $Asu^{7,23}$]--, still line 59, change "hANP7-28)" to --hANP(7-28)--;

line 68, before "mole" insert --times--.

Column 38, line 11, change "mmole" to --times mole--;

line 17, change "(3Synthesis" to --(3) Synthesis--;

line 47, change "NH3" to --$NH_3$--;

line 51, change "[Nle12, Asu7,23]" to --[$Nle^{12}$, $Asu^{7,23}$]--;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 52, change "o-hANP7-28):" to --α-hANP(7-28)--;

line 63, change "(Nle12)" to --(Nle$^{12}$)--, still line 63, change "hANP7-28)" to --hANP(7-28)--;

line 65, change "FvH-hANP7-28)" to --α-hANP(7-28)--;

line 68, change "(Bzl)Phe" to --(Bzl)-Phe--.

Column 39, line 3, change "(114 FvHl," to --(114 µl,--;

line 6, change "Nmethylpyrolidone" to --N-methylpyrrolidone--;

line 7, change "BocCys" to --Boc-Cys--;

line 8, change "FvHl" to --µl--;

line 11, change "thusproduced" to --thus-produced--;

line 17, change "½(Cys 2:small" to --½(Cys)$_2$:small--;

UNITED STATES PATENT AND TRADEMARK OFFICE
CERTIFICATE OF CORRECTION

PATENT NO. : 4,670,540
DATED : June 2, 1987
INVENTOR(S) : Sakakibara

It is certified that error appears in the above-identified patent and that said Letters Patent is hereby corrected as shown below:

line 19, change "(Nle12)" to --(Nle$^{12}$)--;

line 20, change "hANP7-28)" to --hANP(7-28)--;

line 23, change "residue," to --residue.--;

line 24, change "waFvHhed" to --washed--;

line 41, change "HN" to --NH--;

line 64, change "(]" to --(--;

line 68, change "CH$_3$CO$_2$(100 ml)," to --CH$_3$CO$_2$H (100 ml),--.

Column 40, line 2, change "zincpowder" to --zinc-powder--;

line 5, change "recrystalized" to --recrystallized--, still line 5, after "to" insert --give--;

line 30, change "Nmethylpyrolidone" to --N-methylpyrrolidone--, still line 30, change "FvHl," to --µl,--;

line 40, after "to" insert --give--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

It is certified that error appears in the above-identified patent and that said Letters Patent is hereby corrected as shown below:

line 43, change "NH3" to --$NH_3$--;

line 48, change "h-ANP" to --hANP--;

line 51, change "60 µl)" to --(60 µl)--;

line 68, change "AcONH4" to --$AcONH_4$--.

Column 41, line 9, change "50 ml)," to --50 ml).--;

line 12, change "1$CH_3CO_2H$" to --1N $CH_3CO_2H$--;

line 14, change "columnn" to --column--;

line 17, change "mg:" to --mg.--;

line 28, change "o.81," to --0.81--;

line 39, after "added" insert --to--;

line 44, change "N-methylpyroli-" to
--N-methylpyrroli- --.

Column 42, line 7, change "1AcOH," to --1N AcOH,--;

line 12, change "CM-Celluose" to
--CM-Cellulose--;

line 13, change "$NH_4$OAC" to --$NH_4$OAc--;

UNITED STATES PATENT AND TRADEMARK OFFICE
CERTIFICATE OF CORRECTION

PATENT NO. : 4,670,540  
DATED : June 2, 1987  
INVENTOR(S) : Sakakibara

Page 22 of 24

It is certified that error appears in the above-identified patent and that said Letters Patent is hereby corrected as shown below:

line 39, change "ized" to --lized--;

line 43, change "Alal" to --Ala--;

line 52, after ")" (second occurrence) insert --,--;

line 53, change ")," to --)--;

line 56, change "1HCl," to --1N HCl,--;

line 58, change "recrystalized" to --recrystallized--;

line 68, change "N-hexane" to --n-hexane--, still line 68, change "thus-precipiated" to --thus-precipitated--.

Column 43, lines 3 and 4, create a new separate line beginning with "(4)";

line 11, change "mixtured" to --mixed--;

line 32, change "ARg" to --Arg--;

line 65, after "Et$_2$O" insert --,--;

line 66, change ", passed" to --passed--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

It is certified that error appears in the above-identified patent and that said Letters Patent is hereby corrected as shown below:

line 67, change "1AcOH" to --1N AcOH--.

Column 44, line 5, change "NH$_4$AC" to --NH$_4$OAc--;

line 30, change "1HCl," to --1N HCl,--;

line 60, change "1HCl" to --1N HCl--.

Column 45, line 13, change "1.1 eq," to --1.1 eq)--;

line 20, change "DMF," to --DMF.--;

line 29, change " "C " to --C--;

line 42, change "S$_3$.2AcOH.10H$_2$." to --S$_3$·2AcOH·10H$_2$O.--.

Column 46, line 48, change "recrystalized" to --recrystallized--;

line 61, change "5.ON" to --5.0N--.

Column 47, line 37, delete "," (second occurrence);

line 42, change "1AcOH" to --1N AcOH--;

line 43, change "mixtured" to --mixed--;

line 49, change "with 1AcOH." to --washed with 1N AcOH.--;

UNITED STATES PATENT AND TRADEMARK OFFICE
CERTIFICATE OF CORRECTION

PATENT NO. : 4,670,540

DATED : June 2, 1987

INVENTOR(S) : Sakakibara

It is certified that error appears in the above-identified patent and that said Letters Patent is hereby corrected as shown below:

line 65, change "1AcOH." to --1N AcOH.--.

Column 48, line 60, change "6" to --60--.

Column 49, line 4, change "haNP" to --hANP--, still line 4, change "were" to --was--;

line 5, change "were" to --was--;

line 14, delete ",";

line 22, change "bladder, urine" to --bladder. Urine--;

line 23, change "2ml" to --20 ml--;

line 27, change "20 µl" to --20 ml--.

Signed and Sealed this

Twenty-fourth Day of January, 1989

Attest:

DONALD J. QUIGG

*Attesting Officer*         *Commissioner of Patents and Trademarks*